US008999984B2

(12) United States Patent
Mitchell et al.

(10) Patent No.: US 8,999,984 B2
(45) Date of Patent: Apr. 7, 2015

(54) MACROPHAGE MIGRATION INHIBITORY FACTOR ANTAGONISTS AND METHODS OF USING SAME

(75) Inventors: Robert A. Mitchell, Louisville, KY (US); John O. Trent, Louisville, KY (US); Jason B. Meier, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1291 days.

(21) Appl. No.: 12/301,783

(22) PCT Filed: May 24, 2007

(86) PCT No.: PCT/US2007/069672
§ 371 (c)(1),
(2), (4) Date: Sep. 23, 2010

(87) PCT Pub. No.: WO2007/140263
PCT Pub. Date: Dec. 6, 2007

(65) Prior Publication Data
US 2011/0009412 A1    Jan. 13, 2011

Related U.S. Application Data

(60) Provisional application No. 60/808,679, filed on May 26, 2006.

(51) Int. Cl.
| A01N 43/58 | (2006.01) |
| A61K 31/50 | (2006.01) |
| A01N 43/60 | (2006.01) |
| A61K 31/495 | (2006.01) |
| A01N 43/54 | (2006.01) |
| C07D 239/42 | (2006.01) |
| C07D 401/04 | (2006.01) |
| C07D 471/04 | (2006.01) |
| C07D 471/22 | (2006.01) |
| C07D 487/04 | (2006.01) |
| A01N 43/90 | (2006.01) |
| A61K 31/517 | (2006.01) |
| A61K 31/519 | (2006.01) |
| A61K 31/513 | (2006.01) |

(52) U.S. Cl.
CPC .................... A61K 31/513 (2013.01)

(58) Field of Classification Search
USPC ............. 514/269, 247, 248, 256, 257, 258.1
See application file for complete search history.

(56) References Cited

U.S. PATENT DOCUMENTS

| 7,732,540 B2 | 6/2010 | Nakahara et al. |
| 7,863,313 B2 | 1/2011 | Morand et al. |
| 8,293,891 B2 | 10/2012 | Dorsch et al. |
| 2003/0187007 A1 * | 10/2003 | Cao et al. ............ 514/277 |
| 2004/0053843 A1 | 3/2004 | Bucala et al. |
| 2005/0130954 A1 | 6/2005 | Mitchell et al. |
| 2005/0196795 A1 | 9/2005 | Siegler et al. |
| 2007/0281924 A1 | 12/2007 | Gaeta |
| 2008/0317759 A1 | 12/2008 | Bucala et al. |
| 2013/0177552 A1 | 7/2013 | Tezel et al. |

FOREIGN PATENT DOCUMENTS

| EP | 0 767 170 | 4/1997 |
| WO | WO 01/07436 A2 * | 2/2001 |
| WO | WO02/79197 | 10/2002 |
| WO | WO02/079197 | 10/2002 |
| WO | WO 2005/016914 | 2/2005 |
| WO | WO2005/121106 | 12/2005 |
| WO | WO2006/005914 | 1/2006 |
| WO | WO 2008/099000 | 8/2008 |

OTHER PUBLICATIONS

Heyes et al. ("Reactions of phenyllithium with some methylpyrimidine" Journal of the Chemical Society, 1951, 328-331).*
Hitchings ("Division of Biochemistry: A Biochemical Approach to Chemotherapy" Transactions of the New York Academy of Sciences, 23, 1961, 700-708).*
Extended European Search Report corresponding to European Patent Application No. 07811937.7 dated Jun. 17, 2013.
Meyer-Siegler et al. (2005). Further evidence for increased macrophase migration inhibitroy factor expression in prostate cancer, BMC Cancer, vol. 5, No. 1, p. 73 (Jul. 6, 2005).
Al Abed et al. (2005). ISO-1 binding to th tautomerase active site of MIF inhibits its por-inflammatory activity and increases survival in severe sepsis. J Biol Chem. 280:36541-36544.
Brown, J. M. (1993). SR 4233 (tirapazamine): a new anticancer drug expoliting hypoxia in solid tumours. British Journal of Cancer. 67:1163-1170.
Bucala (1996). MIF rediscovered: cytokine, pituitary hormone, and glucocorticoid-induced regulator of the immune response. FASEB J. 14:1607-1613.
Chesney et al. (1999). An essential role for macrophage migration inhibitory factor (MIF) in angiogenesis and the growth of a murine lymphoma. Mol. Med. 5:181-191.
Fingerle-Rowson et al. (2003). The p53-dependent effects of macrophage migration inhibitory factor revealed by gene targeting. Proc. Natl. Acad.Sci. USA. 100:9354-9359.
Hire et al. (2005). Overexpression of macrophage migraiont inhibitory factor induces angiogensis and deteriorates prognosis after radical resection for hepatocellular carcinoma. Cancer. 103:588-598.
International Preliminary Report on Patentability corresponding to International Application No. PCT/US2007/069672 (WO 2007/140263), daed Aug. 7, 2008.
International Search Report corresponding to International Application No. PCT/US2007/069672, dated Aug. 7, 2008.

(Continued)

Primary Examiner — Yong Chong
(74) Attorney, Agent, or Firm — Jenkins, Wilson, Taylor & Hunt, P.A.

(57) ABSTRACT

Methods of inhibiting one or more biological activities of Macrophage migration inhibitory factor (MIF) polypeptides are provided using an MIF inhibitory compound. The methods include therapeutic methods for treating cancers and inflammatory diseases.

7 Claims, 13 Drawing Sheets

(56) References Cited

OTHER PUBLICATIONS

Kamimura et al. (2000). Intracellular distribution of macrophage migration inhibitory factor predicts the prognosis of patients with adenocarcinoma of the lung. Cancer. 89:334-341.
Koong et al. (2000). Candidate Genes for the Hypoxic Tumor Phenotype. Cancer Res. 60:883-887.
Liao et al. (2003). Adhesion-dependent Signaling by Macrophage Migration Inhibitory Factor (MIF). J Biol Chem. 278:76-81.
Markert et al. (2001). Differential gene expression profiling in human brain tumors. Physiol Genomics. 5, 21-33.
Matsunaga et al. (1999). Enzyme activity of macrophage migration inhibitory factor toward oxidized catecholamines. J. Biol. Chem. 274:3268-3271.
McInnes et al. (1988). Interleukin 4 induces cultured monocytes/macrophages to form giant multinucleated cells. J. Exp. Med. 167:598-611.
Meyer-Siegler et al. (2002). Macrophage migration inhibitory factor evaluation compared with prostate specific antigen as a biomarker in patients with prostate carcinoma. Cancer. 94:144-456.
Meyer-Siegler et al. (2006). Inhibition of macrophage migration inhibitory factor or its receptor (CD74) attenuates growth and invasion of DU-145 prostate cancer cells. J Immunol. 177:8730-8739.
Mitchell et al. (1999). Sustained mitogen-activated protein kinase (MAPK) and cytoplasmic phospholispase A2 activation by macrophage migration inhibitory factor (MIF). Regulatory role in cell proliferation and glucocorticoid actin. J Bioi Chem. 274:18100-18106.
Mitchell et al. (2002). Macrophage migration inhibitory factor (MIF) sustains macrophage proinflammatory function by inhibiting p53: regulatory role in the innate immune response. Proc. Natl. Acad. Sci. USA. 99:345-350.
Notification of Transmittal of International Search Report and the Written Opinion of the International Searching Authority, or the Declaration corresponding to International Application No. PCT/US10/50206 dated Mar. 29, 2012.
Office Action corresponding to Chinese Patent Application 200780028307 dated Nov. 8, 2011.
Office Action corresponding to Japanese Patent Application No. 2009-513395 dated Sep. 7, 2012.
Petrenko & Moll (2005). Macrophage migration inhibitory factor MIF interferes with the Rb-E2F pathway. Mol. Cell. 17:225-236.
Ren et al. (2006). Inhibition of tumor growth and metastasis in vitro and in vivo by targeting macrophage migration inhibitory factor in human neuroblastoma. Oncogene. 25(25):3501-8.
Ren et al. (2005). Macrophage migration inhibitory factor stimulates angiogenic factor expression and correlates with differentiation and lymph node status in patients with esophageal squamous cell carcinoma. Ann. Surg. 242:55-63.
Rendon et al. (2007). Regulation of human lung adenocarcinoma cell migration and invasion by MIF: Role of Rac1 GTPase and lipid raft assembly. J Biol Chem. 282(41):29910-8.
Senter et al. (2002). Inhibition of macrophage migration inhibitory factor (MIF) tautomerase and biological activities by acetaminophen metabolites. Proc. Natl. Acad. Sci. USA 99:144-149.
Wilson et al. (2005). Macrophage migration inhibitory factor promotes intestinal tumorigenesis. Gastroenterology.129:1485-1503.
Altenbach et al., "Structure-Activity Studies on a Series of a 2-Aminopyrimidine-Containing Histamine H4 Receptor Ligands," Journal of Medicinal Chemistry, vol. 51, No. 20, pp. 6571-6580 (Jan. 1, 2008).
Babu et al., Synthesis, Antitumor and Antibacterial Activities of Certain Substituted Pyrimidines Bearing Benzofuran Indian Journal of Pharmaceutical Sciences, vol. 66, No. 5, pp. 647-652 (2004).
Bando et al. (2002). Expression of macrophage migration inhibitory factor in human breast cancer: association with nodal spread. Jpn. J. Cancer Res. 93:389-396.
CAS Registration No. 39189-98-5 (Entered Nov. 16, 1984).

del Vecchio et al. (2000). Macrophage migration inhibitory factor in prostatic adenocarcinoma: correlation with tumor grading and combination endocrine treatment-related changes. Prostate. 45:51-57.
Dios et al. (2002). Inhibition of MIF bioactivity by rational design of pharmacological inhibitors of MIF tautornerase activity. J Med. Chem. 45:2410-2416.
European Search Report corresponding to European Patent Application No. 10819534.8-1452/12480235 dated Apr. 8, 2013.
Koong et al. (2000). Pancreatic tumors show high levels of hypoxia Int. J Radiat. Oncol. Bioi Phys. 48:919-922.
Matsuda et al. (1997). Expression of Macrophage Migration Inhibitory Factor in Corneal Wound Healing in Rats. Invest. Ophthalmol. Vis. Sci. 38:1555-1562.
Nicoletti et al. (2005). Macrophage migration inhibitory factor (MIF) seems crucially involved in Guillain-Barre syndrome and experimental allergic neuritis. J Neuroinnmunol. 168:168-174.
Nimavat et al., Synthesis, anticancer, antitubercular and antimicrobial activity of 1-substituted 3-aryl-5-(3'-bromophenyl)-pyrazolines. Indian Journal of Heterocyclic Chemistry, vol. 12, No. 3, pgs. 217-220 (2003).
Notice of Acceptance corresponding to Australian Patent Application No. AU2007267593 dated Mar. 21, 2013.
Notification Concerning Transmittal of International Preliminary Report on Patentability corresponding to Intemational Application No. PCT/US2011/037320 dated Nov. 29, 2012.
Notification of Transmittal of International Search Report and the Written Opinion of the International Searching Authority, or the Declaration corresponding to International Application No. PCT/US2011/037320 dated Oct. 21, 2011.
Office Action Corresponding to U.S. Appl. No. 13/498,036 dated May 14, 2013.
Orita et al. (2001). Coumarin and chromen-4-one analogues as tautomerase inhibitors of macrophage migration inhibitory factor: discovery and X-ray crystallography. J Med. Chem. 44:540-547.
Ouertatani-Sakouhi et al. (2010). Kinetic-based high-throughput screening assay to discover novel classes of macrophase migration inhibitory factor inhibitors. J. Biomol. Screen. 15:347-358.
Pozzi et al. (1992). Human recombinant migration inhibitory factor activates human macrophages to kill tumor cells. Cellular Immunol. 145:372-379.
Suzuki et al., "Structure-activity relationships of pyrazine-based CK2 inhibitors: Synthesis and evaluation of 2,6-disubstituted pyrazines and 4,6-disubstituted pyrimidines," Archiv Der Pharmazie, vol. 341, No. 9, pp. 554-561 (Sep. 1, 2008).
Winner et al. (2008). A novel, macrophage migration inhibitory factor suicide substrate inhibits mofility and growth of lung cancer cells. 68:7253-7257.
Wistow et al. (1993). A macrophage migration inhibitory factor is expressed in the differentiating cells of the eye lens. Proc. Natl. Acad. Sci. USA. 90:1272-1275.
Zhong & Bowen (2006). Antiangiogenesis drug design: multiple pathways targeting tumor vasculature. Curr. Med. Chem. 13:849-862.
Extended European Search Report corresponding to European Patent Applicaton No. 07811937.7 dated Jun. 17, 2013.
Meyer-Siegler et al. (2005). Further evidence for increased macrophase migration inhibitory factor expression in prostate cancer, BMC Cancer, vol. 5, No. 1, p. 73 (Jul. 6, 2005).
Official Action corresponding to European Patent Application No. 10 819 534.8-1452 dated Jun. 20, 2014.
Official Action corresponding to U.S. Appl. No. 13/498,036 dated Apr. 24, 2014.
Official Action corresponding to U.S. Appl. No. 13/498,036 dated Oct. 4, 2013.
Ogawa et al., "An antibody for Macrophase Migration Inhibitory Factor Suppresses Tumour Growth and Inhibits Tumour-Associated Angiogensis," Cytokine, vol. 12, No. 4, pp. 309-314 (2000).
STN CAS RN: 1049024-02-03 (entered Sep. 12, 2008).

* cited by examiner

A.

B.

SEQUENCE LISTING

```
<160> NUMBER OF SEQ ID NOS: 4

<210> SEQ ID NO 1
<211> LENGTH: 115
<212> TYPE: PRT
<213> ORGANISM: Homo sapiens

<400> SEQUENCE: 1

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115

<210> SEQ ID NO 2
<211> LENGTH: 19
<212> TYPE: RNA
<213> ORGANISM: Homo sapiens

<400> SEQUENCE: 2
ccuucuggug gggagaaau                                               19

<210> SEQ ID NO 3
<211> LENGTH: 21
<212> TYPE: DNA
```

```
<213> ORGANISM: Artificial Sequence
<220> FEATURE:
<223> OTHER INFORMATION: artificially-generated siRNA sense strand
      specific for MIF mRNA

<400> SEQUENCE: 3
ccuucuggug gggagaaaut t                                              21

<210> SEQ ID NO 4
<211> LENGTH: 21
<212> TYPE: DNA
<213> ORGANISM: Artificial Sequence
<220> FEATURE:
<223> OTHER INFORMATION: artifically-generated siRNA antisense strand
      specific for MIF mRNA

<400> SEQUENCE: 4
auuucucccc accagaaggt t                                              21
```

MACROPHAGE MIGRATION INHIBITORY FACTOR ANTAGONISTS AND METHODS OF USING SAME

RELATED APPLICATIONS

This application is a U.S. National Stage Application under 35 U.S.C. 371 of PCT Application Ser. No. PCT/US07/69672, filed May 24, 2007, which claims priority under 35 U.S.C. 119 to U.S. Provisional Application Ser. No. 60/808679, filed May 26, 2006, the disclosures of which are incorporated herein by reference in their entirety.

GOVERNMENT INTEREST

This presently disclosed subject matter was made with U.S. Government support under Grant No. 5P20RR018733-02 awarded by The National Institutes of Health, Centers of Biomedical Research Excellence. Thus, the U.S. Government has certain rights in the presently disclosed subject matter.

TECHNICAL FIELD

The presently disclosed subject matter relates to compounds and methods of using the compounds to inhibit biological activities of Macrophage migration inhibitory factor (MIF), including therapeutic methods for the treatment of inflammatory diseases and cancers.

BACKGROUND

The acquisition of migratory and invasive properties by tumor cells is a central and often fatal step in neoplastic disease progression. While normal, non-transformed cells have strict growth factor and adhesive requirements for motility, malignant cells have overcome these requirements through multiple mechanisms including gain of function oncogene mutations, growth factor receptor overexpression and/or constitutive deregulation of extracellular matrix degrading enzymes. Not coincidentally, many solid cancers also possess very low oxygen tensions (Koong et al., 2000b; Buchler et al., 2004).

Hypoxia can induce Macrophage migration inhibitory factor (MIF) expression. It has been demonstrated that MIF expression is increased in pre-malignant, malignant and metastatic tumors. Breast, prostate, colon, brain, skin and lung-derived tumors have all been shown to contain significantly higher levels of MIF message and protein than their non-cancerous cell counterparts. MIF expression closely correlates with tumor aggressiveness and metastatic potential, possibly suggesting an important contribution to disease severity by MIF. MIF has been indirectly implicated in tumor growth and progression by stimulating tumor-dependent stromal processes such as neovascularization. As well, MIF has been implicated in macrophage and lymphocyte activation and survival and may play a role in inflammatory disorder progression.

Thus, certain aggressive tumors appear to possess an important functional requirement for MIF in maintaining optimal growth and progression. Further, MIF may be important in the progression of inflammatory disorders. MIF can therefore be a desirable target for development of therapeutics for the treatment of cancer. As such, there is presently an unmet need for therapeutic molecules that specifically target MIF and modulate one or more biological activities of MIF for the treatment of cancers and inflammatory disorders.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides compounds for use in inhibiting a biological activity of a Macrophage inhibitory factor (MIF) polypeptide by contacting the MIF with the compound. In some embodiments, the compounds have a structure of Formula (I):

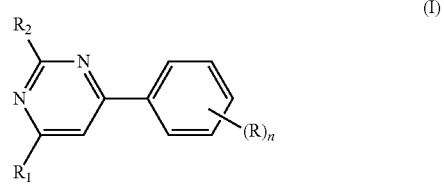

wherein:
each R is independently H, halo, OH, alkyl, substituted alkyl, aryl, amino, or carboxyl;
$R_1$ is H, halo, OH, alkyl, substituted alkyl, or aryl;
$R_2$ is H, halo, OH, alkyl, substituted alkyl, aryl, or amino; and
n is an integer from 0 to 5.

In some embodiments, $R_1$ is iodo. In a particular embodiment, the compound is 4-iodo-6-phenylpyrimidine or an analog or derivative thereof.

In some embodiments, the compound forms a stable interaction with at least a methionine at the second N-terminal residue (Met-2) of the MIF polypeptide. Further, in some embodiments, the compound forms a stable interaction (e.g., a covalent bond) with at least a proline at the first N-terminal residue (Pro-1) of the MIF polypeptide. MIF (e.g., SEQ ID NO:1) comprises a homotrimer of monomers A, B, and C, and monomer A can comprise the Met-2 (Met-A2) to which the compound stably interacts. In some embodiments, the compound further forms a stable interaction with one or more of Lys-32, Pro-33, Tyr-36, His-62, Ser-63, Ile-64, Lys-66, Tyr-95, Met-101, Val-106, Trp-108 and Phe-113 of the MIF polypeptide.

As disclosed herein, MIF biological activity inhibition can result in indirect inhibition of Hypoxia-Inducible Factor 1α (HIF-1α) biological activity through affects on HIF-1α stability. As such, in some embodiments of the presently disclosed subject matter, a method of inhibiting HIF-1α polypeptide biological activity is provided. The method comprises in some embodiments, contacting a MIF polypeptide with a compound disclosed herein having a structure of Formula (I), which in turn results in inhibition of one or more biological activities of HIF-1α. In some embodiments, inhibiting HIF-1α polypeptide activity inhibits transcriptional activity of the HIF-1α polypeptide. Further, in some embodiments of the method, inhibiting HIF-1α polypeptide activity inhibits angiogenesis, radiation-resistance, or both in a cell expressing the HIF-1α, such as for example a hypoxic cancer cell. In some embodiments, the MIF polypeptide is contacted with a compound disclosed herein in conjunction with treating the cell with radiation, a chemotherapeutic agent, or both.

In some embodiments of the presently disclosed subject matter, a method of inhibiting or preventing oncogenic activity of a cell is provided. In some embodiments, the method comprises contacting a cell with a compound disclosed herein having a structure of Formula (I). In some embodiments, inhibiting or preventing oncogenic activity comprises inhibiting migration, invasion, cell survival, anchorage-independent growth, angiogenesis, or combinations thereof of the cell. In some embodiments, inhibiting or preventing oncogenic activity comprises inhibiting activity of a Rho GTPase family member (e.g., Rac1 and/or RhoA) through inhibition of the MIF polypeptide by the compound. In some embodiments, the cell is a cancer cell selected from the group consisting of lung cancer, head and neck cancer, pancreatic cancer, renal cell cancer, prostate cancer, glioblastoma, and mammary adenocarcinoma.

In some embodiments of the presently disclosed subject matter, a method of treating or reducing the risk of recurrence of a cancer in a subject is provided. In some embodiments, the method comprises administering to the subject an effective amount of a compound disclosed herein having a structure of Formula (I). In some embodiments, treating the cancer comprises inhibiting migration, invasion, cell survival, anchorage-independent growth, angiogenesis, or combinations thereof of the cancer. Further, in some embodiments, the compound is administered to the subject in conjunction with treating the cancer with radiation, chemotherapy, or both. In some embodiments, the chemotherapy comprises a hypoxia-activated compound, such as for example tirapazamine. In some embodiments, the cancer is a cancer selected from the group consisting of lung cancer, head and neck cancer, pancreatic cancer, renal cell cancer, prostate cancer, glioblastoma, and mammary adenocarcinoma.

In some embodiments of the presently disclosed subject matter, a method of treating an inflammatory disorder in a subject is provided. In some embodiments, the method comprises administering to the subject an effective amount of a compound disclosed herein having a structure of Formula (I). In some embodiments, the inflammatory disorder is selected from the group consisting of atopic dermatitis, arthritis, proliferative vascular disease, acute respiratory distress syndrome (ARDS), cytokine-mediated toxicity, sepsis, septic shock, psoriasis, interleukin-2 toxicity, asthma, MIF-mediated conditions, autoimmune disorders, tumor growth or angiogenesis. Further, in some embodiments the autoimmune disorder is selected from the group consisting of rheumatoid arthritis, insulin-dependent diabetes, multiple sclerosis, graft versus host disease, and lupus syndromes.

The presently disclosed subject matter further provides in some embodiments, an antisense polynucleotide comprising a nucleotide sequence having binding specificity for SEQ ID NO:2. In some embodiments, the antisense polynucleotide is a small interfering RNA (siRNA). Further, in some embodiments, the antisense nucleotide sequence comprises SEQ ID NO:3. Further, in some embodiments, the antisense nucleotide sequence comprises SEQ ID NO:4. Still further, in some embodiments, the presently disclosed subject matter provides a method of inhibiting expression of a MIF polypeptide in a cell or tissue, comprising contacting the cell or tissue with the antisense polynucleotide having binding specificity for a target sequence within MIF (e.g., SEQ ID NO:2).

Accordingly, it is an object of the presently disclosed subject matter to provide MIF antagonists and methods of using same. This object is achieved in whole or in part by the presently disclosed subject matter.

An object of the presently disclosed subject matter having been stated hereinabove, and which is achieved in whole or in part by the presently disclosed subject matter, other objects and advantages will become evident to those of ordinary skill in the art after a study of the following description of the presently disclosed subject matter, figures, and non-limiting examples.

BRIEF DESCRIPTION OF THE DRAWINGS

FIG. 3A is a photograph of an immunoblot showing MIA-Paca-2 cells transfected with NS or MIF siRNA, incubated 48 hours, then cells placed under normoxic or hypoxic conditions, and supernatant collected after 24 hours. FIG. 3B is a bar graph showing results from transfected MIA-Paca-2 cells incubated for 16 hours in either hypoxia or normoxia, then cDNA synthesized from cell RNA, and real-time PCR used to determine levels of MIF transcript. FIG. 3C is a photograph of a Northern blot showing mRNA expression in HIF-1α$^{+/+}$ and HIF-1α$^{-/-}$ mouse embryonic fibroblasts challenged with 1% hypoxia and MIF. FIG. 3D is a graph showing assessment for plasma MIF levels by ELISA from healthy donors and pancreatic adenocarcinoma patients collected prior to chemotherapeutic treatment were assessed. *, P<0.05 by Student's t test (two-tailed).

FIG. 4C is a graph showing real time PCR analysis of VEGF mRNA levels from control and MIF-depleted cells exposed to hypoxia for different times.

FIG. 5A: MIA-PaCa-2 cells were incubated with CoCl$_2$ for 4 h and extracts were analyzed by western blotting for MIF, CSN5 and β-actin or immunoprecipitated with a CSN5 antibody and immunoprecipitates were evaluated for MIF interaction by immunoblotting of MIF. FIG. 5B: siRNA transfected MIA-PaCa-2 were incubated with or without 150 μM CoCl$_2$ for 4 h.

Whole cell extracts and nuclear extracts were obtained in parallel. Whole cell extracts were immunoprecipitated using anti-CSN5. Nuclear extracts and co-immunoprecipitates were analyzed for HIF-1α by immunoblotting. FIG. 5C: siRNA transfected MIA-PaCa-2 cells were incubated with or without 10 μM MG-132 for 6 hours. Both whole cell extracts and nuclear extracts were obtained. Whole cell extracts were immunoprecipitated with anti-CSN5. Nuclear extracts and co-immunoprecipitates were analyzed by western blotting for HIF-1α while a small fraction of the whole cell lysate was assessed for total CSN5.

In FIGS. 9A and 9B, MIA-PaCa pancreatic adenocarcinoma cells were used. In FIG. 9C, MIF+/+ and MIF-/- mouse embryonic fibroblasts were evaluated.

In FIG. 10A, 500 nM rMIF was pre-mixed for 30 seconds with the indicated inhibitor concentrations followed by the addition of 2 mM final concentration of L-dopachrome methyl ester substrate. 5 minutes later OD 475 was measured spectrophotometrically (tautomerization leads to colorless substrate) and resulting data graphed. In FIG. 10B, 2×10$^5$ A549 cells transfected or pre-incubated with the indicated inhibitor or DMSO were added to the upper chamber of collagen coated transwell chambers. 16 hours later cells in the upper chamber were removed by swabbing and the bottom of the membranes were stained with crystal violet, solubilized, read at OD 570, and resulting data graphed.

FIG. 14C (top panel) shows a scheme of the capture assay used for assessing MIF/MIF receptor small molecule binding inhibitors and MIF site specific mutant/receptor binding. FIG. 14A is a graph of data from the assay where CD74 coated plates were pre-incubated with the indicated concentrations of native MIF (MIF), denatured MIF or P1G MIF followed by the addition of 0.2 μM biotin-hrMIF. FIG. 14B is a graph of data from the assay where 1.0 μM of denatured MIF (dMIF), native MIF (MIF) or anti-CD74 were pre-incubated with soluble CD74 for 30 mins before adding 0.2 μM biotin-hrMIF. For inhibitors, 0.1 μM ISO-1 or 4-iodo-6-phenyl pyrimidine (Cmp16) were pre-incubated for 30 mins with 0.2 μM biotin-hrMIF before adding mixture to CD74 coated plate. In both FIGS. 14A and 14B, plates were developed 2 hours later by incubating Streptavidin-AP followed by PnPP and measurement at OD$_{405}$.

BRIEF DESCRIPTION OF THE SEQUENCE LISTING

Figure 1:
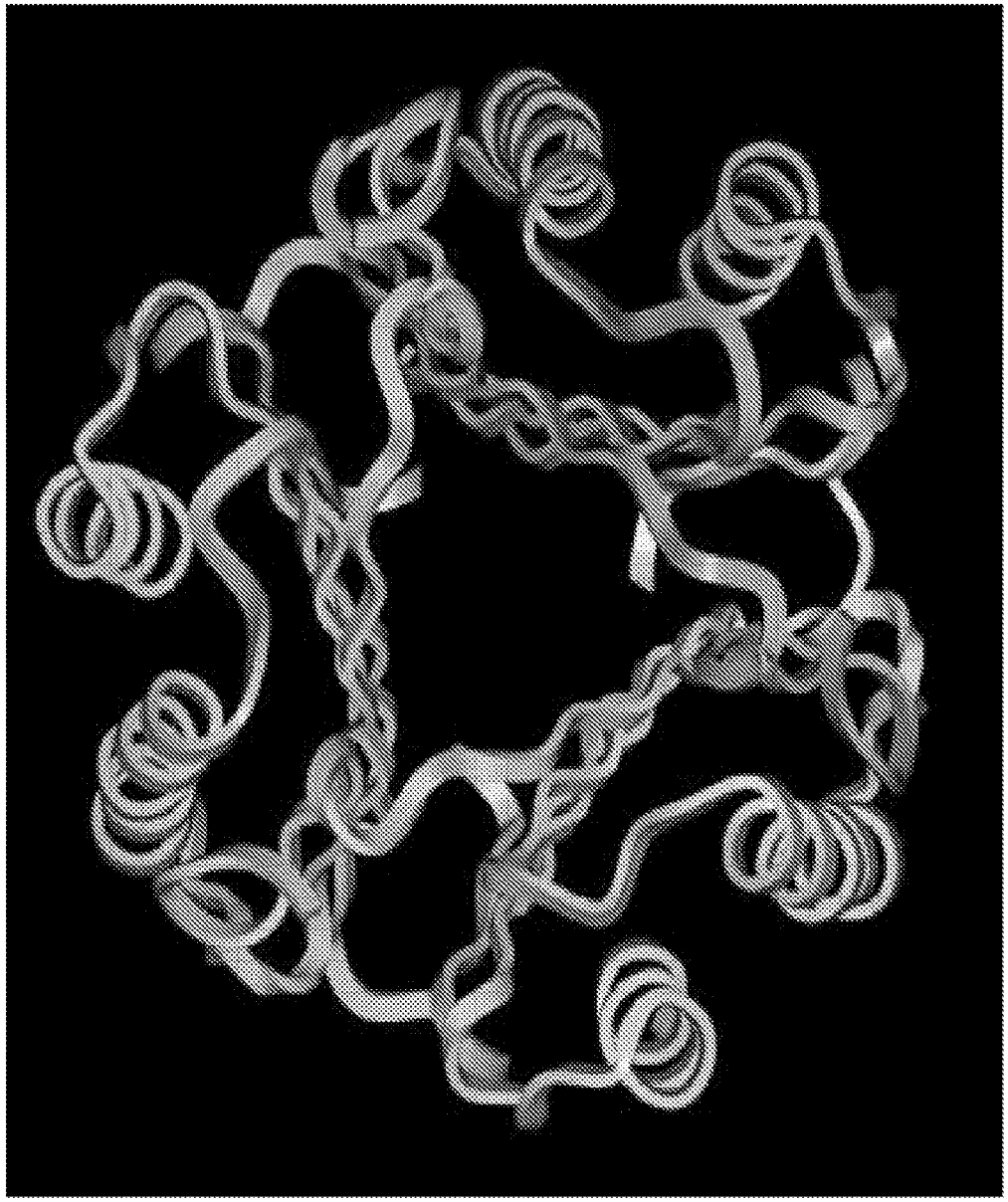
FIG. 1 is a drawing showing the X-ray crystallographic-determined three-dimensional structure of human MIF, which exists as a homotrimer.

SEQ ID NO: 1 is a *Homo sapiens* MIF polypeptide sequence.

SEQ ID NO: 2 is a siRNA Target Sequence from MIF.

SEQ ID NO: 3 is the sense strand of an MIF-targeted siRNA sequence.

SEQ ID NO: 4 is the antisense strand of an MIF-targeted siRNA sequence.

DETAILED DESCRIPTION

The details of one or more embodiments of the presently disclosed subject matter are set forth in the accompanying description below. Other features, objects, and advantages of the presently disclosed subject matter will be apparent from the description, figures, and claims. All publications, patent applications, patents, and other references noted herein are incorporated by reference in their entirety. Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. In case of conflict, the present specification, including definitions, will control.

Many cancers are highly aggressive and produce invasive malignancies. Pancreatic cancer is exemplary of one type of aggressive and invasive cancer, having an overall five year survival rate averaging a dismal 3-5% (Garcea et al., 2005). Not coincidentally, these aggressive cancers reportedly possess very low oxygen tensions (Koong et al., 2000b; Buchler et al., 2004). Hypoxia can induce Macrophage migration inhibitory factor (MIF; see FIG. 1) expression in cancer cells and MIF plasma levels are elevated in cancer patients. MIF expression is also positively regulated by growth factors, extracellular matrix and oncogenic stimuli in both normal and transformed cells (Mitchell et al., 1999; Liao et al., 2003; Petrenko et al., 2003).

MIF is over-expressed in a large variety of human neoplasias. Pancreatic, breast, prostate, colon, brain, skin and lung-derived tumors have all been shown to contain significantly higher levels of MIF message and protein than their non-cancerous cell counterparts (Winner et al., 2007; Meyer-Siegler et al., 1998; Bando et al., 2002; Takahashi et al., 1998; Markert et al., 2001; Shimizu et al., 1999; Kamimura et al., 2000). Several of these studies also report that MIF expression closely correlates with tumor aggressiveness and metastatic potential, suggesting an important contribution to cancer severity by MIF (del Vecchio et al., 2000; Kamimura et al., 2000; Meyer-Siegler et al., 2002).

As such, it can be desirable to attempt to mediate inhibition of these MIF-mediated tumor phenotypes with molecules that target MIF, and in particular the MIF catalytic active site. For example, in a recent report an anti-MIF small molecule was found to inhibit prostate cancer cell migration and xenograft tumor growth and vascularity only in cells that express the cognate cell surface receptor of MIF (Meyer-Siegler et al., 2006).

The presently disclosed subject matter provides compounds that are newly-identified anti-MIF antagonists, which can modulate MIF biological activities and exhibit both catalytic and biologic inhibitory activities that are 5-10× more potent than previously tested compounds. Thus, the presently disclosed subject matter provides compounds, and methods of using the compounds for inhibiting biological activities of MIF, including therapeutic methods for the treatment of inflammatory diseases and cancers.

I. Macrophage Migration Inhibitory Factor

MIF is one of the earliest described cytokines, and is an immunoregulatory protein with a wide variety of biological activities (for reviews see: Swope et al., 1999; Metz et al., 1997; and Bucala, 1996). Originally, MIF was found to be secreted by activated lymphoid cells, to inhibit the random migration of macrophages, and to be associated with delayed-type hypersensitivity reactions (George et al., 1962; Weiser et al., 1981; Bloom et al., 1966; David, 1966). MIF was also shown to enhance macrophage adherence, phagocytosis and tumoricidal activity (Nathan et al., 1973; Nathan et al., 1971; Churchill et al., 1975). Unfortunately, many of the early MIF studies used mixed-culture supernatants that were shown later to contain other cytokines, such as IFN-γ and IL-4, that also have macrophage migration inhibitory activity (McInnes et al., 1988; Thurman et al., 1985). The availability of recombinant MIF has allowed for confirmation of these biological activities, and for the identification of additional activities.

Recombinant human MIF was originally cloned from a human T cell library (Weiser et al., 1989), and was shown to activate blood-derived macrophages to kill intracellular parasites and tumor cells in vitro, to stimulate IL-1β and TNFα expression, and to induce nitric oxide synthesis (Weiser et al. 1991; Pozzi et al., 1992; Weiser et al., 1992; Cunha et al., 1993). While the conclusions available from several of these early reports are confounded by the presence of a bioactive mitogenic contaminant in the recombinant MIF preparations used, the potent pro-inflammatory activities of MIF have been established in other studies that do not suffer from this complicating factor (reviewed in Bucala, 1996).

More recent MIF studies have capitalized on the production of recombinant MIF in purified form as well as the development of MIF-specific polyclonal and monoclonal antibodies to establish the biological role of MIF in a variety of normal homeostatic and pathophysiological settings (reviewed in Rice et al., 1998). Among the insights of these later reports has been the recognition that MIF not only is a cytokine product of the immune system, but also is a hormone-like product of the endocrine system, particularly the pituitary gland. This work has underscored the potent activity of MIF as a counter-regulator of the anti-inflammatory effects of the glucocorticoids (both those endogenously released and those therapeutically administered), with the effect that the normal activities of glucocorticoids to limit and suppress the severity of inflammatory responses are inhibited by MIF. The endogenous MIF response is thus seen as a cause or an exacerbative factor in a variety of inflammatory diseases and conditions (reviewed in Donnelly et al. 1997).

MIF is now known to have several other biological functions beyond its well-known association with delayed-type hypersensitivity reactions. For example, as noted above, MIF released by macrophages and T cells acts as a pituitary mediator in response to physiological concentrations of glucocorticoids (Bucala, 1996). This leads to an overriding effect of glucocorticoid immunosuppressive activity through alterations in TNF-α IL-1β, IL-6, and IL-8 levels. Additional biological activities of MIF include the regulation of stimulated T cells (Bacher et al., 1996), the control of IgE synthesis (Mikayama et al., 1993), the functional inactivation of the p53 tumor suppressor protein (Hudson et al., 1999), the regulation of glucose and carbohydrate metabolism (Sakaue et al., 1999), and the attenuation of tumor cell growth and tumor angiogenesis (Chesney et al., 1999); Shimizu et al., 1999).

Figure 2:
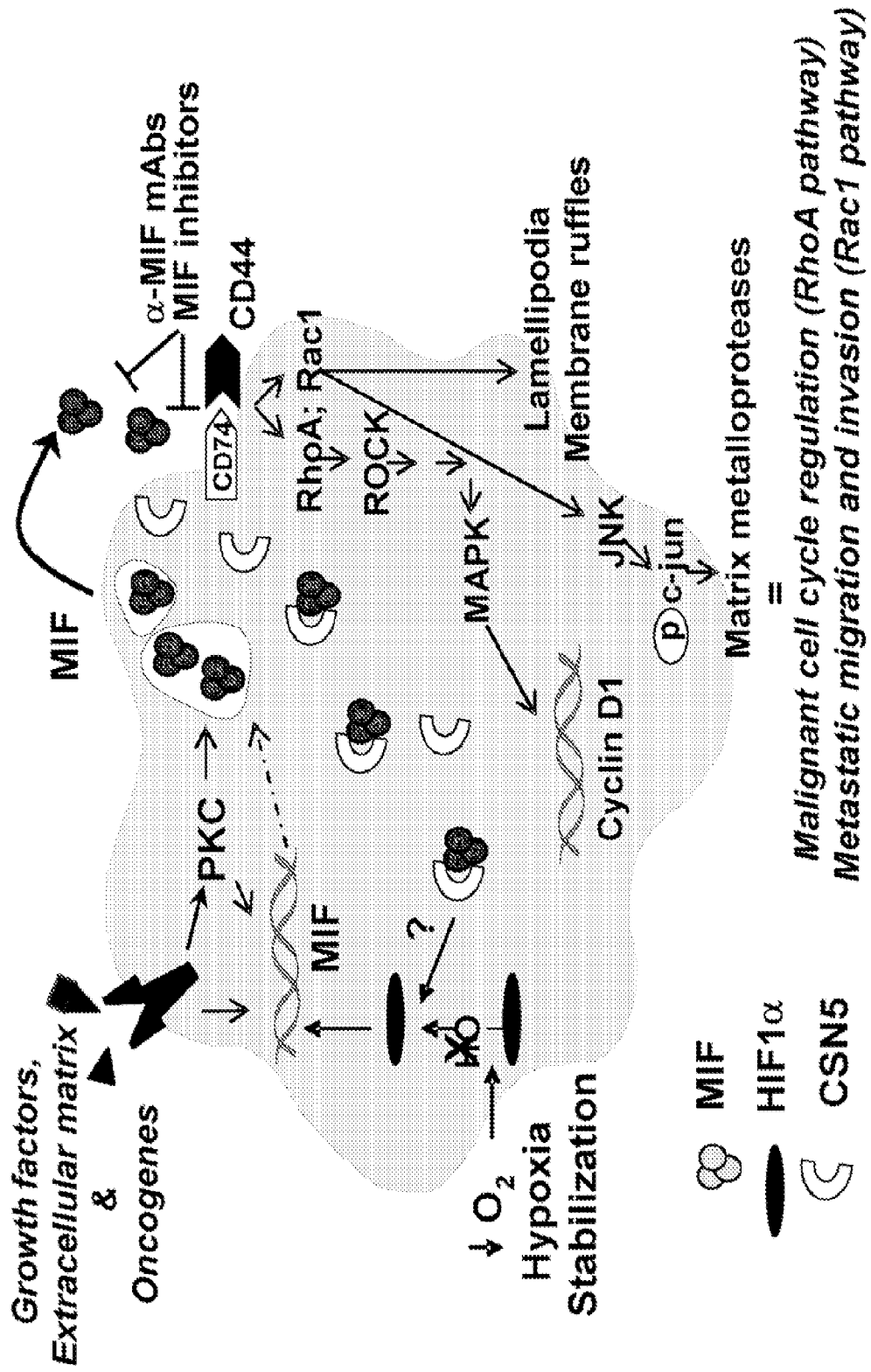
FIG. 2 is a schematic drawing showing the proposed scheme of MIF-dependent signaling to cell growth, migration/invasion and HIF stabilization. MIF expression/secretion is induced by growth factors/extracellular matrix (ECM). Extracellular MIF binds to its receptor, CD74 which interacts with CD44 (35). Active CD44 can then promote RhoA and/or Rac1 GTPase activation. In the RhoA pathway, Rho kinase-dependent sustained MAP kinase activation leads to cyclin D1 transcription and retinoblastoma inactivation (36). MIF stimulated Rac1 activation can lead to lamellipodia formation and MMP production allowing directed migration and invasion (22). Finally, MIF internalization and subsequent binding to CSN5 promotes hypoxia-induced HIF-1α stabilization.

The present inventors have further determined, and as disclosed in detail herein, MIF is necessary for Hypoxia-Inducible Factor (HIF) stabilization induced by hypoxia. Without wishing to be bound by any particular theory, MIF expression by mitogenic and oncogenic pathways may provide a set point for hypoxia-induced HIF stabilization and subsequent hypoxic adaptation (FIG. 2). Once stabilized, HIF can potentially then dictate the over-expression of MIF in hypoxic regions of a developing neoplasm, setting up an amplification loop consisting of HIF and MIF.

Consistent with a requirement for MIF in hypoxic adaptation, MIF may also play a role in tumor-associated angiogenesis. Specifically, MIF intratumoral expression strongly correlates with angiogenic growth factor expression, tumor vessel density and risk of recurrence after resection (Ren et al., 2005; Wilson et al., 2005; Shun et al., 2005; Hira et al., 2005; Chesney et al., 1999; White et al., 2001). These findings are consistent with a study demonstrating that MIF-deficient mice crossed to adenomatous polyposis coli ($Apc^{Min/+}$) "oncomice" show significant reductions in both the number and size of adenomas that correspond to greatly diminished tumor microvessel density (Wilson et al., 2005).

MIF shares significant sequence homology (36% identity) with D-dopachrome tautomerase. This led to the discovery that MIF has enzymatic activity and catalyzes the tautomerization of the non-physiological substrates D-dopachrome (Rosengren et al., 1996) and L-dopachrome methyl ester (Bendrat et al., 1997. Additionally, phenylpyruvic acid and p-hydroxyphenylpyruvic acid (Rosengren et al., 1997, and 3,4-dihydroxyphenylaminechrome and norepinephrinechrome (Matsunaga et al., 1999), are MIF substrates, although it is not known if tautomerization of any of these agents comprises a natural function for MIF.

The three-dimensional crystal structure of human MIF reveals that the protein exists as a homotrimer (See FIG. 1; Lolis et al., 1996) and is structurally related to 4-oxalocrotonate tautomerase, 5-carboxymethyl-2-hydroxymuconate, chorismate mutase, and to D-dopachrome tautomerase (Swope et al., 1998; Sugimoto et al. 1999). The crystal structure has been reported for the complex formed between human MIF and p-hydroxyphenylpyruvic acid (Lubetsky et al., 1999). It was found that the substrate binds to a hydrophobic cavity at the amino terminus and interacts with at least Pro-1, Lys-32, and Ile-64 in one of the subunits, and with Tyr-95 and Asn-97 in an adjacent subunit. Similar interactions between murine MIF and (E)-2-fluoro-p-hydroxycinnamate have been reported (Taylor et al., 1999). The N-terminal proline of MIF (Pro-1) appears to be an important residue for enzymatic activity, as site-directed mutagenesis that substitutes a serine for this proline (P1S) is devoid of D-dopachrome tautomerase activity (Bendrat et al., 1997). Similarly, a proline to glycine (P1G) MIF mutant is also catalytically null for both D-dopachrome and HPP tautomerase activities (Lubetsky et al., 1999; Swope et al., 1998).

Despite its activity being first described over 30 years ago, a classical, membrane bound receptor for MIF has only recently been described (Leng et al., 2003). Through expression cloning and functional analysis, it was demonstrated that CD74 is a high affinity binding protein for extracellular MIF (Leng et al., 2003). MIF was shown to bind to the extracellular domain of CD74, a type II transmembrane protein, and initiate MIF-dependent signaling to ERK MAP kinase, prostaglandin E2 ($PGE_2$) production and cell replication. Because the cytosolic portion of CD74 is small and contains no classical signaling or scaffold domains, the CD74/MIF complex is thought to relay its activation signal through other cell surface molecules. One such molecule is the tumor-associated antigen, CD44, that is activated by heterotypic binding of chondroitin sulfated CD74 (Naujokas et al., 1993). A recent report from Shih et al. now describe that CD44 is necessary for MIF-CD74 signal transduction (Shi et al., 2006) (See FIG. 2).

Recent studies demonstrated a function for extracellular MIF in the steady state activation of Rho GTPase family members leading to cell growth and migratory phenotypes (Swant et al., 2005; Rendon et al., 2006). These MIF-mediated effects are thought to be linked to CD74/CD44 initiated signaling (Summarized in FIG. 2). Further, as shown in the present examples, MIF inhibitory compounds disclosed herein can block binding of MIF to CD74 thereby inhibiting the proximal signal transduction initiated by extracellular MIF.

Several additional proteins have also been identified by yeast 2 hybrid screening to interact with MIF (Jung et al., 2001; Wadgaonkar et al., 2005; Potolicchio et al., 2003; Kleemann et al., 2000). One of these proteins, Jab1/CSN5, has also been shown to physically interact with HIF-1α and pVHL directly (Bemis et al., 2004). Previously, MIF was shown to modulate CSN5 function and subsequent CSN5-dependent effects on p27 degradation, JNK activation and AP-1-mediated transcription (Kleemann et al., 2000). Interestingly, this report found that extracellular MIF modulates the activities of intracellular CSN5. The authors described the binding of extracellular MIF to intracellular CSN5 and, presumably after receptor-mediated endocytic internalization, MIF binds to and inhibits CSN5-dependent functions (Kleemann et al., 2000).

Studies by the present inventors along with colleagues (Winner et al., 2007), and studies of others (Leng et al., 2003) strongly support the supposition that extracellular MIF can functionally regulate intracellular Jab1/CSN5 functions. Further, the data presented in the Examples and in other studies demonstrate that exogenous MIF can rescue HIF destabilization induced by MIF siRNA, but small molecule inhibitors can block the effect of extracellular MIF (Winner et al., 2007). Without wishing to be bound by theory, because both active site inhibitors of MIF and neutralizing MIF monoclonal antibodies block MIF-dependent HIF stabilization while also blocking MIF/MIF receptor binding, it is possible that this internalization step is relevant to at least some of the inhibitory activities of the presently disclosed MIF inhibitory compounds.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The term "biological activity" as used herein with reference to a particular biologically-active molecules, such as a polypeptide (e.g., Macrophage migration inhibitory factor (MIF) or Hypoxia-Inducible Factor 1α (HIF-1α)) is inclusive of any biological or enzymatic activity by the molecule on another molecule or substrate. For example, with reference to MIF, "biological activity" includes but is not limited to inhibition of Th1 lymphocyte responses (Abe et al. 2001 *J Immunol* 166:747-53), transcription regulation (e.g., of cyclin D1 expression (Liao et al. 2003 *J Biol Chem* 278:76-81; Swant et al. 2005 *J Biol Chem* 280:23066-72)), cell migration promotion, cell invasion promotion, anchorage-independent growth promotion, angiogenesis promotion (Chesney et al. 1999 *Mol Med* 5:181-91; Shimizu et al. 1999 *Biochem. Biophys. Res. Commun.* 264:751-8; Ogawa et al. 2000 *Cytokine* 12:309-14; White et al. 2001 *J. Immunol.* 166:7549-55; White et al. 2003 *Clin. Cancer Res.* 9:853-60), promotion of HIF-1α expression, arachidonic acid metabolism, E2F transcription factor regulation (Petrenko & Moll 2005 *Mol. Cell* 17:225-36), Rb inactivation (Liao et al. 2003 *J Biol Chem* 278:76-81; Swant et al. 2005 *J Biol Chem* 280:23066-72), and p53 inhibition (Hudson et al. 1999 *J. Exp. Med.* 190:1375-82; Mitchell et al. 2002 *Proc. Natl. Acad. Sci. U.S. A* 99:345-50). With reference to MIF, "biological activity" is also inclusive of enzymatic activities, such as for example tautomerase activity.

The terms "cancer" and "cancer cell" are used interchangeably herein and refer generally to a group of diseases characterized by uncontrolled, abnormal growth of cells. In some forms of cancer, the cancer cells can spread locally or through the bloodstream and lymphatic system to other parts of the body ("metastatic cancer"). Certain intractable forms of cancer have been observed to be very hypoxic and resistant to particular therapies, such as for example radiation therapy. As disclosed herein, MIF plays a direct or indirect role in facilitating several oncogenic activities, including migration, invasion, cell survival, anchorage-independent growth, hypoxic adaptation and angiogenesis, that contribute to cancer cell survival, growth and metastases. As such, the presently disclosed subject matter provides MIF-inhibiting compounds for the treatment of susceptible cancers. For example, the therapeutic compounds disclosed herein can be utilized to treat head and neck cancers and pancreatic cancers, as these cancers are very hypoxic due to HIF-1α activity. MIF contributes to HIF-1α expression and activity and therefore the MIF-inhibitory activities of the therapeutic compounds can inhibit oncogenic activities of these cancers. Renal cell cancer and prostate cancer also depend on HIF-1α activity for oncogenesis and thus MIF-inhibitory compounds can inhibit these activities via MIF inhibition. Further, lung cancers (e.g., lung adenocarcinoma) and glioblastomas are both very metastatic and require MIF activities for metastatic behaviors (e.g., cell invasion and migration). As such, MIF-inhibitory compounds can decrease oncogenic and metastatic activity in these cancers. Still further, mammary carcinomas require cyclin D1 expression for oncogenic activities and MIF is necessary for efficient cyclin D1 expression (see Appendix). Thus, MIF-inhibitory compounds can inhibit oncogenic and metastatic activities in these cancers as well.

As used herein, the term "effective amount" means a dosage sufficient to provide treatment for the condition or disease state being treated. This can vary depending on the subject, the disease and the treatment being effected.

"Hypoxia-Inducible Factor 1" or "HIF-1" is a transcription factor and is important for cell survival in hypoxic conditions, including in cancer cells. HIF-1 is composed of the $O_2$ and growth factor-regulated subunit HIF-1α, and the constitutively expressed HIF-1β subunit (arylhydrocarbon receptor nuclear translocator, ARNT), both of which belong to the basic helix-loop-helix (bHLH)-PAS (PER, ARNT, SIM) protein family. At present, in the human genome, three isoforms of the subunit of the transcription factor HIF have been identified: HIF-1, HIF-2 (also referred to as EPAS-1, MOP2, HLF, and HRF), and HIF-3. Under normoxic conditions, HIF-1α is targeted to ubiquitinylation and is rapidly degraded by the proteasome. However, under hypoxic conditions, HIF-1α is stabilized, in part through interaction with MIF and/or MIF-regulated CSN5, and translocates to the nucleus where it hetero-dimerizes with HIF-1β. The resulting activated HIF-1 drives the transcription of over 60 genes, including MIF, important for cell adaptation and survival under hypoxia.

The term "inflammatory disorder", as used herein refers to disorders involving the immune system, including disorders characterized by inflammation. Exemplary inflammatory disorders include but are not limited to atopic dermatitis, arthritis, proliferative vascular disease, acute respiratory distress syndrome (ARDS), cytokine-mediated toxicity, sepsis, septic shock, psoriasis, interleukin-2 toxicity, asthma, MIF-mediated conditions, autoimmune disorders, tumor growth or angiogenesis. "Inflammatory disorder", as the term is used herein is inclusive of autoimmune disorders. Exemplary autoimmune disorders include but are not limited to rheumatoid arthritis, insulin-dependent diabetes, multiple sclerosis, graft versus host disease, and lupus syndromes.

The terms "inhibitor" and "antagonist" refer to a chemical substance that inhibits, that is inactivates or decreases, the biological activity of a polypeptide such as for example a MIF polypeptide.

The terms "operably linked" and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "polynucleotide" refers to a polymer of two or more nucleic acids. The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) Nucleic Acid Res 19:5081; Ohtsuka et al. (1985) *J Biol Chem* 260:2605-2608; Rossolini et al. (1994) *Mol Cell Probes* 8:91-98). The terms "nucleic acid" or "nucleic acid sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

As used herein, the term "stable interaction" with reference to an interaction of one or more amino acid residues of MIF and a compound disclosed herein refers to a chemical interaction between the moieties, including but not limited to covalent bonding and non-covalent bonding such as Van der Waals interactions, electrostatic forces, hydrogen bonding, or combinations thereof. In particular, disclosed herein is the interaction of an inhibitory compound (e.g., compounds of Formula (I), including 4-iodo-6-phenylpyrimidine and any analogs and derivatives thereof) with amino acids of MIF, such as Met-2 of MIF. "Met-2" refers to the second amino acid residue, in this case a methionine, of a MIF polypeptide (e.g., a human MIF (SEQ ID NO:1; GenBank Accession No. NP_002406, herein incorporated by reference in its entirety)) as counted from the N-terminus of the MIF polypeptide. Likewise, certain inhibitory compounds of MIF disclosed herein can stably interact with one or more additional MIF residues such as, but not limited to, "Pro-1" (e.g., a covalent interaction), "Lys-32", "Pro-33", and "Tyr-36", which refers to the first amino acid (a proline), the thirty-second amino acid (a lysine), the thirty-third amino acid (a proline), and the thirty-sixth amino acid (a tyrosine) of a human MIF, respectively, as counted from the MIF N-terminus.

III. Mif-Inhibitory Compounds

Human MIF/HPP and MIF/inhibitor co-crystal structures have identified a substrate-binding hydrophobic cavity that lies between two adjacent subunits of the functional MIF homotrimer (Lubetsky et al., 1999; Taylor et al., 1999). Initial attempts to rationally design small compound inhibitors of MIF bioactivity based on this substrate binding site have provided some success, although these compounds do not inhibit biological activities of MIF to the extent desired for clinical effectiveness. (Senter et al., 2002; Lubetsky et al., 2002; Dios et al., 2002). Without wishing to be bound by any particular theory, the present inventors theorized that the disruption of this substrate binding site by structure-based inhibitors can efficiently neutralize MIF binding to its cell surface receptor thereby blocking its receptor-initiated signaling (FIG. 2). Other studies have targeted the Pro A1 residue found on the side of the hydrophobic pocket. However, results disclosed herein suggest that targeting the Met A2 residue that lies at the base of this substrate-binding hydrophobic cavity yields superior MIF catalytic and biological inhibitors.

Of the MIF biological antagonists reported thus far (Senter et al., 2002; Lubetsky et al., 2002; Dios et al., 2002), ISO-1 (S, R-3-(4-hydroxyphenyl)-4,5-dihydro-5-isoxazole acetic acid methyl ester), appears to be the most potent (Lubetsky et al., 2002; Nicoletti et al., 2005; Al Abed et al., 2005; Meyer-Siegler et al., 2006). Studies reveal that this compound, at high concentrations, can block MIF-dependent malignant phenotypes (see Examples and Rendon et al., 2006; Meyer-Siegler et al., 2006). The ability of ISO-1 to inhibit prostate cancer cell invasion, tumor volume and angiogenesis requires the presence of the cognate MIF receptor, CD74.

The presently disclosed subject matter provides structurally-unique MIF inhibitory compounds, disclosed in detail hereinbelow, that are substantially more potent in blocking MIF-dependent enzymatic activity, receptor binding, HIF-1α stabilization, cell migration and anchorage independence than ISO-1 and related compounds (see Examples). One unique aspect of the presently disclosed compounds is that a pyrimidine ring is responsible for occupying the active site with the iodo group situated at the Met A2 position at the base of the active site (see Examples). The presently disclosed compounds are as effective as siRNA-mediated knockdown of MIF and 3-5× more effective than other MIF antagonist compounds in blocking hypoxia-induced HIF-1α accumulation and subsequent phenotypes.

As such, the presently disclosed subject matter provides compounds that form stable interactions with MIF and can thereby inhibit biological activities of MIF. In some embodiments, the compounds can form stable interactions with at least a methionine at the second N-terminal residue (Met-2) of the MIF polypeptide. In particular embodiments, the compounds form stable interactions with a Met-2 of monomer A of the MIF monotrimer. In some embodiments, the compounds can further form stable interactions with one or more of Pro-1, Lys-32, Pro-33, Tyr-36, His-62, Ser-63, Ile-64, Lys-66, Tyr-95, Met-101, Val-106, Trp-108 and Phe-113 of the MIF polypeptide. In particular embodiments, the compounds form covalent bonds with the Pro-1 of MIF.

In some embodiments, the MIF inhibitory compound has a structure of Formula (I):

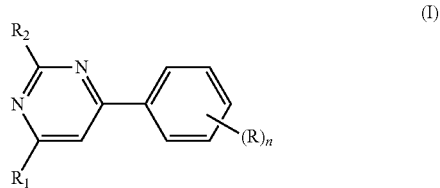

wherein:
each R is independently H, OH, alkyl, substituted alkyl, amino, or carboxyl;
$R_1$ is H, halo, OH, alkyl, or substituted alkyl;
$R_2$ is H, OH, alkyl, substituted alkyl, or amino; and
n is an integer from 0 to 5.

A named "R" (e.g., R, $R_1$, and $R_2$) group will generally have the structure that is recognized in the art as corresponding to a group having that name, unless specified otherwise herein. For the purposes of illustration, certain representative "R" groups as set forth herein are defined below. These definitions are intended to supplement and illustrate, not preclude, the definitions that would be apparent to one of ordinary skill in the art upon review of the present disclosure.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, aryl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl (forming a hydroxyalkyl, e.g., $(CH_2)_n$—OH, wherein n is 1-20), nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group —$CH_2HC=CH_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

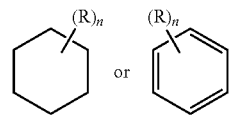

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. When n is 0, the structure is unsubstituted, and each atom on the ring is bonded to neighbor atoms on the ring and hydrogen atoms only. For example, when the structure is phenyl and n is zero, the carbon atoms on the phenyl ring are bonded to one hydrogen each, although in keeping with structure drawing conventions in the art of organic chemistry, the hydrogen atoms are not shown. Each R group, if more than one, is substituted on an available carbon of the ring structure rather than on another R group. For example, the structure:

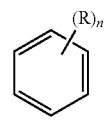

wherein n is an integer from 0 to 2 comprises compound groups including, but not limited to:

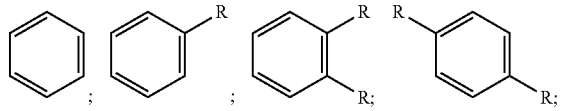

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

In some embodiments, the compounds described by the presently disclosed subject matter contain a linking group. As used herein, the term "linking group" comprises a chemical moiety, such as a furanyl, phenylene, thienyl, and pyrrolyl radical, which is bonded to two or more other chemical moieties, in particular aryl groups, to form a stable structure.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include, but are not limited to, cyclopropyl, cyclobutyl, cyclopentyl, cyclohexyl, cycloheptyl, and the like. Further, the cycloalkyl group can be optionally substituted with a linking group, such as an alkylene group as defined hereinabove, for example, methylene, ethylene, propylene, and the like. In such cases, the cycloalkyl group can be referred to as, for example, cyclopropylmethyl, cyclobutylmethyl, and the like. Additionally, multicyclic cycloalkyl rings include adamantyl, octahydronaphthyl, decalin, camphor, camphane, and noradamantyl.

"Alkoxyl" or "alkoxyalkyl" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and

R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —$NH_2$ group.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

Figure 6:
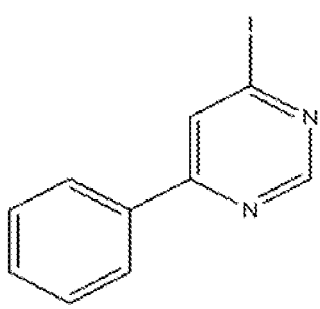
FIG. 6 is a drawing of an exemplary MIF inhibitory compound of the presently disclosed subject matter, 4-iodo-6-phenylpyrimidine.

In some particular embodiments, the compound that stably interacts with MIF and inhibits MIF biological activities is 4-iodo-6-phenylpyrimidine (see FIG. 6) or an analog or derivative thereof. Structure-based drug design (SBDD), for example, can be used to identify additional MIF inhibitory compounds having a structure of Formula I. The success of SBDD for effective compound development is well documented. It has contributed to the introduction of 50 compounds into clinical trials and to numerous drug approvals (Jorgensen, 2004). Virtual screening is one aspect of SBDD and is a computational technique that can prescreen vast databases of small molecule structures against a three-dimensional structure to see which fit, or dock, into the chosen site. This can reduce the actual physical screening for compounds of interest many orders of magnitude. There are a variety of methods available, both rigid and flexible docking (DOCK (Ewing et al., 2001), Autodock (Morris et al., 1998), GOLD (Jones et al., 1997), Ligandfit (Accelrys), Ludi (Accelrys), FlexX (Tripos), FlexX-pharm (Tripos), FlexE (Tripos) and Glide (Schrodinger) and there are a variety of scoring, or ranking, methods used such as FlexX (Rarey et al., 1996), SCORE (Ewing et al., 2001), Chemscore (Eldridge et al., 1997), Ludi (Bohm, 1992) and PLP (Gehlhaar et al., 1995), GOLD (Jones et al., 1997), and Ligandfit (Venkatachalam et al., 2003).

Past efforts at screening for potential MIF inhibitors, used the N-terminal proline as the central target residue for inhibition. In contrast, the presently disclosed subject matter utilizes in some embodiments a virtual screening strategy that focuses on identifying compounds that target methionine at position MET A2 (i.e., MIF monomer A, position 2, with reference to the human crystal structure of MIF which is made up of A, B and C monomers to form a catalytically active trimer). This is a noteworthy distinction over prior efforts as demonstrated by the presently disclosed MIF inhibitory compounds, which can be ~5× more potent than previously identified MIF inhibitory compounds. The present inventors focused on this active site residue, in part, because; 1) it resides at the base of the hydrophobic binding pocket adjacent to the N-terminal proline that actually resides on the side of the pocket (Sun et al., 1996); and, 2) prior studies have shown that disrupting this hydrophobic substrate-binding pocket by insertion of a single amino acid residue adjacent to Met A2 leads to a complete loss of enzymatic and biologic activity (Lubetsky et al., 2002). Thus, additional exemplary compounds having a structure of Formula I encompassed by the presently disclosed subject matter and having MIF inhibitory properties can be identified without undue experimentation utilizing the presently disclosed novel screening and testing methods.

IV. Methods of Use

The presently disclosed subject matter provides MIF inhibitory compounds, as disclosed hereinabove in detail, that can target MIF's catalytic active site and act as MIF biologic antagonists, which can have inhibitory activity of MIF biological functions multiple times more effective than previously-described MIF inhibitors. For example, in some embodiments, the presently disclosed MIF inhibitory compounds can inhibit hypoxia-induced HIF-1α stabilization at concentrations 5× lower than those needed by other MIF inhibitory compounds. Without wishing to be bound by any particular theory of operation, the presently disclosed MIF inhibitory compounds appear to exhibit potencies that correlate closely with their ability to block binding of MIF to its cell surface receptor. Thus, and again without wishing to be bound by theory, biologic inhibitory activities of the presently disclosed MIF antagonists appear to depend at least in part on their ability to prevent binding of MIF to its cell surface receptor, CD74.

As such, the presently disclosed subject matter provides methods of inhibiting a biological activity of a MIF polypeptide comprising contacting the MIF polypeptide with a MIF inhibitory compound disclosed herein. Exemplary biological activities of MIF that can be inhibited by the presently disclosed compounds include inhibition of Th1 lymphocyte, transcription regulation (e.g., of cyclin D1 expression), cell migration promotion, cell invasion promotion, anchorage-independent growth promotion, angiogenesis promotion, promotion of HIF-1α stabilization, arachidonic acid metabolism, E2F transcription factor regulation, Rb inactivation, and p53 inhibition.

Further, as disclosed herein, MIF biological activity inhibition can result in indirect inhibition of Hypoxia-Inducible Factor 1a (HIF-1α) biological activity. As such, in some embodiments of the presently disclosed subject matter, a method of inhibiting HIF-1α polypeptide biological activity is provided. The method comprises in some embodiments, contacting a MIF polypeptide with a MIF inhibitory compound disclosed herein, which in turn results in inhibition of one or more biological activities of HIF-1α. In some embodiments, inhibiting HIF-1α polypeptide activity inhibits transcriptional activity of the HIF-1α polypeptide. Further, in some embodiments of the method, inhibiting HIF-1α polypeptide activity inhibits angiogenesis, radiation-resistance, or both in a cell expressing the HIF-1α, such as for example a hypoxic cancer cell. In some embodiments, the MIF polypeptide is contacted with a compound disclosed herein in conjunction with treating the cell with radiation, a chemotherapeutic agent, or both.

IV.A. Therapeutic Methods

The identification of more biologically active drugs targeting MIF, for example MIF receptor binding, may represent a novel therapeutic approach for inhibiting oncogenic activities of cancer cells and treating cancer that acts at least in part by inhibiting hypoxic adaptation. Related thereto, therapeutic methods are provided by the presently disclosed subject matter utilizing the MIF inhibitory compounds disclosed herein. Therapeutic methods disclosed herein include methods of inhibiting or preventing oncogenic activity of a cell, treating a cancer, and reducing the risk of recurrence of a cancer. Further, the MIF inhibitory compounds disclosed herein can inhibit MIF biological activities related to immune and inflammatory system functioning. Therefore, the present MIF inhibitory compounds can further be utilized to treat inflammatory and autoimmune disorders.

In some embodiments, the therapeutic methods include methods of inhibiting or preventing oncogenic activity of a cell. The methods comprise contacting a cell with an MIF inhibitory compound disclosed herein (e.g., a compound of Formula (I)). In some embodiments, the cell is a cancer cell selected from the group consisting of lung cancer, head and neck cancer, pancreatic cancer, renal cell cancer, prostate cancer, glioblastoma, and mammary adenocarcinoma.

Inhibiting or preventing oncogenic activity can comprise inhibiting migration, invasion, cell survival, anchorage-independent growth, angiogenesis, or combinations thereof of the cell. A critical group of effectors downstream of mutated oncogenes or constitutively active growth factor receptors is the family of Rho GTPase enzymes. As illustrated in FIG. 2, MIF plays a role in Rho family oncogenic activities. Of the three main family members, Rac, Rho and Cdc42, Rac is arguably the most important in promoting and maintaining an invasive phenotype. For example, in addition to promoting actin cytoskeletal reorganization, Rac is also necessary for non-small cell lung cancer matrix metalloprotease expression and subsequent invasive behavior. Thus, in some embodiments, inhibiting or preventing oncogenic activity comprises inhibiting activity of a Rho GTPase family member (e.g., Rac1 and/or RhoA) through inhibition of the MIF polypeptide by the compound.

In some embodiments of the presently disclosed subject matter, a method of treating, or reducing the risk of recurrence, of a cancer in a subject is provided. In some embodiments, the method comprises administering to the subject an effective amount of a MIF inhibitory compound disclosed herein. In some embodiments, treating the cancer comprises inhibiting migration, invasion, cell survival, anchorage-independent growth, angiogenesis, or combinations thereof of the cancer. In some embodiments, the cancer is a cancer selected from the group consisting of lung cancer, head and neck cancer, pancreatic cancer, renal cell cancer, prostate cancer, glioblastoma, and mammary adenocarcinoma.

In some embodiments of the cancer treatment methods, the compound is administered to the subject in conjunction with treating the cancer with radiation, chemotherapy, or both. For example, in some embodiments, the chemotherapy utilized in conjunction with administration of MIF antagonists disclosed herein can comprise a hypoxia-activated chemotherapeutic compound. "Hypoxia-activated" compounds are small molecule compounds activated to a toxic radical form only under hypoxic conditions. Such low oxygen levels are common in solid tumors, as previously disclosed herein. Thus, hypoxia-activated compounds are activated to their toxic forms preferentially in the hypoxic areas of solid tumors. One non-limiting example of a hypoxia-activated chemotherapeutic compound that can be administered in combination with a MIF antagonist disclosed herein is tirapazamine (3-amino-1,2,4-benzotriazine-1,4 dioxide). See, e.g., Zeman et al. (1986) *Int J Radiat Oncol Biol Phys* 12 (7): 1239-42 and Gandara et al. (2002) *Semin Oncol* 29 (1 Suppl 4): 102-9 for a further description of tirapazamine and hypoxia-activated compounds as cancer therapeutics in general.

As noted, MIF biological activities also include immune function regulation and MIF plays a role in many inflammatory disorders. As such, in some embodiments of the presently disclosed subject matter, a method of treating an inflammatory disorder in a subject is provided. In some embodiments, the method comprises administering to the subject an effective amount of a MIF inhibitory compound disclosed herein. In some embodiments, the inflammatory disorder is selected from the group consisting of atopic dermatitis, arthritis, proliferative vascular disease, acute respiratory distress syndrome (ARDS), cytokine-mediated toxicity, sepsis, septic shock, psoriasis, interleukin-2 toxicity, asthma, MIF-mediated conditions, autoimmune disorders, tumor growth or angiogenesis. Further, in some embodiments the autoimmune disorder is selected from the group consisting of rheumatoid arthritis, insulin-dependent diabetes, multiple sclerosis, graft versus host disease, and lupus syndromes. However, treatable inflammatory disorders are not limited to those specifically disclosed herein.

IV.B. Subjects

With respect to the therapeutic methods of the presently disclosed subject matter, a "subject" as the term is used herein in some embodiments refers to a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

IV.C. Formulations

Suitable methods for administering to a subject a therapeutic compound in accordance with the methods of the present subject matter include but are not limited to systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance compound accumulation at a target site (see, e.g., U.S. Pat. No. 6,180,082). The particular mode of administration used in accordance with the methods of the present subject matter depends on various factors, including but not limited to the compound and/or carrier employed, the severity of the condition to be treated, and mechanisms for metabolism or removal of the compound following administration.

A therapeutic composition as described herein preferably comprises a composition that includes a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions used in the methods can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods known in the art. For example, an MIF antagonist disclosed herein can be formulated as a pH stabilized core having an enteric or delayed release coating which protects the MIF antagonist until it reaches the desired location in the gastrointestinal tract.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

V. RNA Interference

The presently disclosed subject matter provides antisense polynucleotides that have binding specificity for portions of the MIF coding sequence and can be used to modulate (e.g., inhibit) the expression of a MIF polynucleotide in a cell or tissue by contacting the cell or tissue with the antisense polynucleotide. In some embodiments, the antisense polynucleotide comprises a nucleotide sequence having binding specificity for the polynucleotide sequence CCTTCTGGTGGGGAGAAAT (SEQ ID NO:2) of MIF. In some embodiments, the siRNA comprises a sense strand comprising the polynucleotide sequence CCUUCUG-GUGGGGAGAAAUdTdT (SEQ ID NO:3). Further, in some embodiments, the siRNA comprises an antisense strand comprising the polynucleotide sequence AUUUCUCCCCAC-CAGAAGGdTdT (SEQ ID NO:4).

The term "modulate" as used herein can refer to a change in the expression level of a gene, or a level of RNA molecule or equivalent RNA molecules encoding one or more proteins or protein subunits, or activity of one or more proteins or protein subunits is up-regulated or down-regulated, such that expression, level, or activity is greater than or less than that observed in the absence of the modulator. For example, the term "modulate" can mean "inhibit" or "suppress", but the use of the word "modulate" is not limited to this definition.

The term "RNA" refers to a molecule comprising at least one ribonucleotide residue. By "ribonucleotide" is meant a nucleotide with a hydroxyl group at the 2' position of a 13-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically-synthesized nucleotides or deoxynucleotides. These altered RNAs can be referred to as analogs or analogs of a naturally occurring RNA.

The term "antisense polynucleotide" can refer to "small interfering RNA", "short interfering RNA", "small hairpin RNA", "siRNA", and "shRNA", which are used interchangeably and refer to any nucleic acid molecule capable of mediating RNA interference (RNAi) or gene silencing. See e.g., Bass et al, 2001; Elbashir et al., 2001a; and PCT International Publication Nos. WO 00/44895, WO 01/36646, WO 99/32619, WO 00/01846, WO 01/29058, WO 99/07409, and WO 00/44914.

In one embodiment, the antisense polynucleotide is an siRNA and comprises a double stranded polynucleotide molecule comprising complementary sense and antisense regions, wherein the antisense region comprises a sequence complementary to a region of a target nucleic acid molecule (for example, a nucleic acid molecule encoding MIF), such that when allowed to hybridize to the target nucleic acid molecule, the siRNA binds with specificity to the target nucleic acid molecule. In another embodiment, the siRNA comprises a single-stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

The presently disclosed subject matter takes advantage of the ability of short, double stranded RNA molecules to cause the down regulation of cellular genes, a process referred to as RNA interference. As used herein, "RNA interference" (RNAi) refers to a process of sequence-specific post-transcriptional gene silencing mediated by a small interfering RNA (siRNA). See Fire et al., 1998 and U.S. Pat. No. 6,506,559, each of which is incorporated by reference herein in its entirety. The process of post-transcriptional gene silencing is thought to be an evolutionarily conserved cellular defense mechanism that has evolved to prevent the expression of foreign genes (Fire, 1999).

RNAi might have evolved to protect cells and organisms against the production of double-stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., 2001b).

RNAi has been described in several cell types and organisms. Fire et al., 1998 described RNAi in *C. elegans*. Wianny & Zernicka-Goetz, 1999 disclose RNAi mediated by dsRNA in mouse embryos. Hammond et al., 2000 were able to induce RNAi in *Drosophila* cells by transfecting dsRNA into these cells. Elbashir et al. 2001a demonstrated the presence of RNAi in cultured mammalian cells including human embryonic kidney and HeLa cells by the introduction of duplexes of synthetic 21 nucleotide RNAs.

Other studies have indicated that a 5'-phosphate on the target-complementary strand of a siRNA duplex facilitate siRNA activity and that ATP is utilized to maintain the 5'-phosphate moiety on the siRNA (Nykanen et al., 2001).

Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2, 359, 180).

Other references disclosing the use of dsRNA and RNAi include PCT International Publication Nos. WO 01/75164 (in vitro RNAi system using cells from *Drosophila* and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi), each of which are incorporated herein by reference in their entireties.

In some embodiments, the presently disclosed subject matter utilizes RNAi to at least partially inhibit expression of MIF. Inhibition is preferably at least about 10% of normal expression amounts. In some embodiments, the method comprises contacting a target cell with an antisense polynucleotide in an amount sufficient to inhibit expression of MIF. In some embodiments, the target cell is present in a subject, and the RNA is introduced into the subject.

The RNA can have a double-stranded region comprising a first strand comprising a ribonucleotide sequence that corresponds to the coding strand of the gene encoding the target protein (e.g., MIF) and a second strand comprising a ribonucleotide sequence that is complementary to the first strand. The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases.

One skilled in the art will recognize that any number of suitable common techniques can be used to introduce the RNAs into a target cell. In some embodiments, a vector encoding the RNA is introduced to the target cell. For example, the vector encoding the RNA can be transfected into the target cell and the RNA is then transcribed by cellular polymerases.

In some embodiments, a recombinant virus comprising a nucleic acid encoding the RNA can be produced. Introducing the RNA into a target cell then comprises infecting the target cell with the recombinant virus. Cellular polymerases transcribe the RNA resulting in expression of the RNA within the target cell. Engineering recombinant viruses is well known to those having ordinary skill in the art. One of skill would readily appreciate the multiple factors involved in selecting the appropriate virus and vector components needed to optimize recombinant virus production for use with the presently disclosed subject matter without the necessity of further detailed discussion herein. Details of recombinant virus production and use can be found in published PCT International Application No. PCT/US02/22010, herein incorporated by reference in its entirety. Alternatively, a commercial kit for producing recombinant viruses can be used, such as for example, the pSILENCER ADENO 1.0-CMV SYSTEM™ (Ambion, Austin, Tex., USA).

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Hypoxia Induces MIF Expression and Secretion in a HIF-1α-Dependent Manner

Figure 3:
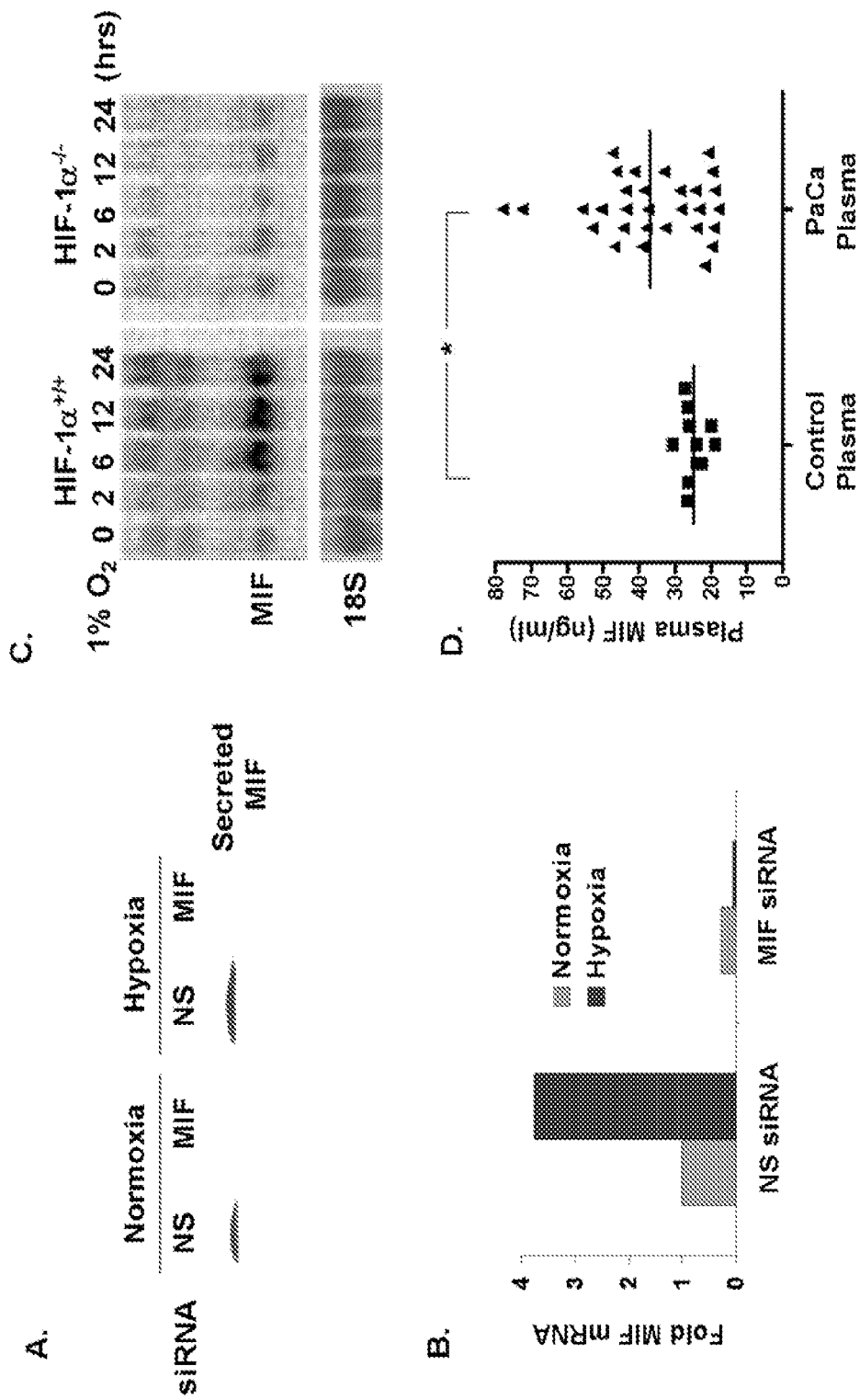
FIGS. 3A-3D show data demonstrating that MIF transcription and secretion are enhanced by hypoxia, and subjects with pancreatic adenocarcinoma have elevated levels of plasma MIF.

MIF expression is increased in response to low oxygen tension, as demonstrated in cancer cell lines (Bacher et al., 2003; Koong et al., 2000a). Because pancreatic cancers are reportedly very hypoxic (Koong et al., 2000b), a study was initiated to investigate MIF regulation by hypoxia in human pancreatic cancer cell lines. Results indicate that two human pancreatic adeno-carcinoma cell lines, MIA-PaCa-2 (FIG. 3) and PANC-1 are sensitive to hypoxia-induced transcriptional regulation of MIF. Specifically, it was found that MIF secretion (FIG. 3A) and transcription (FIG. 3B) is markedly increased when subjected to a low oxygen environment. Accompanying FIG. 3 are data from cells that had been transfected with short interfering RNA (siRNA) oligos designed against human MIF. Additionally, mouse embryonic fibroblasts (MEFs) from HIF-1α-deficient mice (Ryan et al., 1998; Zundel et al., 2000) were found to be severely refractory to hypoxia-induced MIF transcription (FIG. 3C).

Tumor hypoxia has been described as an excellent prognostic indicator for neoplastic disease in general (Janssen et al., 2005; Menon and Fraker, 2005; Shannon et al., 2003) and pancreatic cancer, specifically (Koong et al., 2000b). In an attempt to correlate the presently disclosed in vitro findings (FIGS. 3A and 3B) to a clinical setting, MIF plasma levels were next measured in patients previously diagnosed with pancreatic adenocarcinoma. A study was established to assess MIF levels in plasma samples from normal control donors and patients with cancer of the pancreas who had yet to undergo any cancer therapy. As shown in FIG. 3D, the median MIF levels for control plasma was 24.8 ng/ml while pancreatic carcinoma patient's mean MIF levels were 36.8 ng/ml (P=0.0382 by two tailed Student's t test). These results are the first to show a positive correlation between MIF levels in the plasma and patients with pancreatic adenocarcinoma.

Example 2

MIF is necessary for hypoxia-induced HIF-1α stabilization and Subsequent Transcription some transcriptional targets of HIF-1α can possibly also regulate the expression and/or stabilization of HIF-α (Epstein et al., 2001; Hagen et al., 2003). The results in Example 1 demonstrate that MIF is a target of HIF-1α gene transcription and is strongly induced by hypoxia. Because of the well documented modulation of hypoxia-induced gene expression by HIF-1α it was investigated whether HIF-1α stabilization by hypoxia was sensitive to loss of MIF.

MIF-specific siRNA was transfected into MIA-Paca-2 cells before being incubated in 0.2% $O_2$ (anoxia) for 16 hours. As shown in FIG. 4A, depletion of MIF by siRNA resulted in a loss of cytoplasmic MIF expression by greater than 90% while not affecting β-actin expression. While HIF-1α was efficiently stabilized in the nuclei by anoxia treatment in mock transfected or control siRNA transfected cells, cells lacking MIF were completely deficient in HIF-1α stabilization (FIG. 4A). To more thoroughly investigate the requirements for MIF in hypoxia-mediated HIF-1α stabilization, a time course evaluating MIF containing vs. deficient pancreatic adenocarcinoma cells exposed to 1% $O_2$ (hypoxia) was performed. The findings revealed that there is a strong requirement for MIF in hypoxia-mediated HIF stabilization at all time points evaluated (FIG. 4B) and that this requirement is at the level of HIF protein stability (see also Winner et al., 2007).

Hypoxia-induced expression of vascular endothelial cell growth factor (VEGF) is a critical step in the malignant progression of tumors and is the target of multiple anti-cancer modalities (Zhong and Bowen, 2006). Because of the potency of this pro-angiogenic growth factor in stimulating tumor-associated angiogenesis, it has been reported that disruption of the expression or signaling of VEGF is anti-tumorigenic (Grunstein et al., 1999; Tsuzuki et al., 2000; Graeven et al., 2001). To determine whether hypoxia-induced VEGF transcription was attenuated by MIF depletion, Real Time PCR analysis on MIF competent or deficient cells exposed to hypoxia for differing times was performed. The data indicate that maximal hypoxia-induced VEGF transcription is heavily reliant upon MIF (FIG. 4C), which may explain why MIF is so vitally important for tumor-associated angiogenesis (Chesney et al., 1999; Wilson et al., 2005; White et al., 2001; Shun et al., 2005). In a broader sense, these studies indicate that pancreatic tumorigenic potential—suggested to be globally influenced by hypoxia-initiated signaling (Koong et al., 2000b)—may be dependent upon the presence of MIF.

Example 3

MIF binds to CSN5 in pancreatic adenocarcinoma cells and MIF Depletion Results in a Loss of CSN5 Binding and Stabilization of HIF-1α

Figure 5:
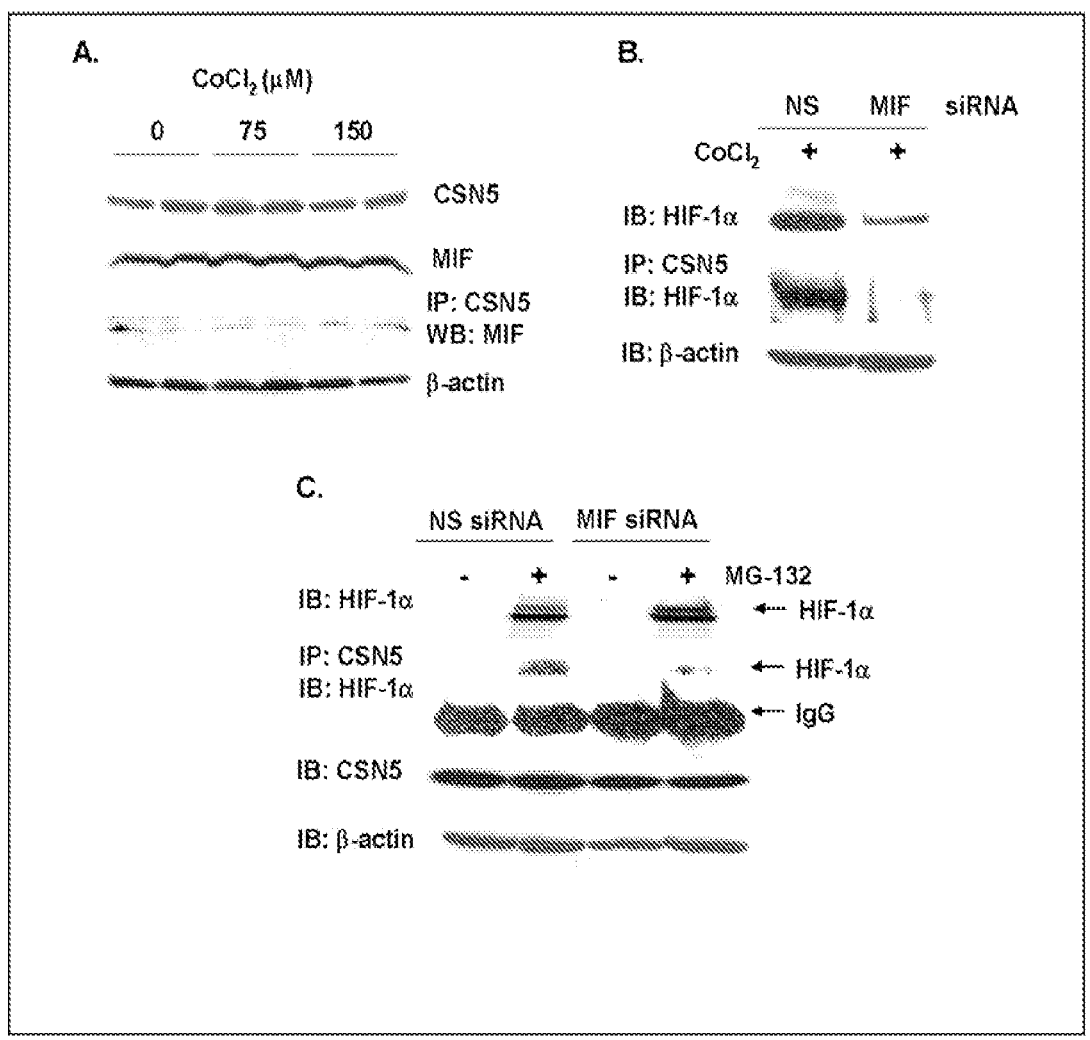
FIGS. 5A-5C show data demonstrating that MIF interacts with CSN5 and promotes CSN5/HIF-1α interaction.

Because MIF is reported to modulate the function of CSN5 (Kleemann et al., 2000) and CSN5 was recently shown to be necessary for hypoxia-induced HIF-1α stabilization (Bemis et al., 2004), it was next sought to determine if there was any functional connection between MIF and CSN5 in HIF-1α stabilization. To determine if MIF interacts with CSN5 in pancreatic adenocarcinoma cells, co-immunoprecipitations were performed from lysates of cells exposed to varying concentrations of $CoCl_2$. As shown in FIG. 5A, MIF was efficiently co-immunoprecipitated with CSN5 under all conditions tested with a very moderate increase observed in the presence of $CoCl_2$. This increase in MIF/CSN5 interaction was very reproducible and suggests that there may be some level of regulation that influences MIF/CSN5 intracellular binding.

Because binding of CSN5 acts to functionally stabilize HIF-1α (Bemis et al., 2004), it was next determined whether loss of MIF disrupts binding of HIF-1α to CSN5. Co-immunoprecipitation of the CSN5/HIF-1α complex from untreated and $CoCl_{1-2}$-treated MIF-competent and depleted cells revealed that loss of MIF significantly decreased CSN5 binding to HIF-1α induced by PHD inhibition (FIG. 5B). Although there appeared to be a significant difference between the HIF-1α expression in cell lysates (top panel) versus the amount of HIF-1α being pulled down with CSN5 (middle panel), the possibility that the observed loss of CSN5/HIF-1α interaction in MIF-depleted cells was simply due to overall loss of HIF-1α stabilization could not be ruled out.

To address this issue, a proteasome inhibitor was used to artificially stabilize HIF-1α in MIF-containing and MIF-depleted cells. Importantly, MIF-depleted pancreatic carcinoma cells treated with proteasome-inhibitor contained an equivalent amount of stabilized HIF-1α as cells containing MIF (FIG. 5C). This finding suggests a role for MIF in modulating HIF-1α protein degradation and not transcription or translation.

Cell lysates were then assessed for CSN5/HIF-1α interactions in MG-132-mediated HIF-1α stabilized cells. Intriguingly, MG-132-treated MIF containing cells contained a significant amount of CSN5 bound HIF-1α while MIF-deficient cells contained only a small fraction of this CSN5/HIF-1α complex (FIG. 5C). It is noteworthy that CSN5 levels were unchanged by MIF status (FIG. 5C). These results suggest a direct functional role for MIF in CSN5-dependent HIF-1α stabilization.

Combined, these findings reveal a novel co-regulatory axis between MIF and HIF-1α in pancreatic adenocarcinoma cells. The data indicate that MIF expression and secretion is enhanced by hypoxia in a HIF-1α-dependent manner and, more importantly, that steady state MIF is necessary for hypoxia-induced HIF-1α stabilization. The results further suggest that MIF contributes to HIF-1α stabilization by facilitating CSN5 binding to HIF-1α and is consistent with prior reports describing MIF as a functional regulator of CSN5-bioactions (Kleemann et al., 2000).

These studies further suggest that MIF represents an excellent target to design anti-neoplastic pharmacologic agents. Not only is MIF necessary for determining HIF-1α stability in hypoxic environments, subsequent stabilization of HIF acts to increase the expression and secretion of MIF leading to increased tumor cell motility as well as enhanced proliferative potential. The next set of Examples disclose investigations on the identification and testing of the presently disclosed-MIF inhibitory compounds and demonstrate they are active in blocking hypoxia-induced stabilization of HIF-1α and subsequent malignant phenotypes.

Example 4

Virtual Screening and Testing of Small Molecule MIF Inhibitory Compounds

The only reported virtual screen against MIF utilized an early version of DOCK with the Advanced Chemistry Development (ACD) libraries and found compounds in the library that were similar to the normal substrates and some with very high activities (enrichment rate of ~3%) (Orita et al., 2001). For the present studies, a novel MIF inhibitor template that could be subsequently modified was devised and tested. The base of the MIF substrate binding pocket, Met A2, was targeted and the computer program LUDI (Accelrys, San Diego, Calif., U.S.A.) was used, which considers hydrogen-bond donors and acceptors and aliphatic nature (parameters: 8 Å radius with no linkage, or rotatable bonds, 5000 fits, 300 lowest hits to be stored, aliphatic_aromatic and electrostatic_ check options, using the ACD library), in a rigid body dock. The sdf files from the ACD (Elsevier MDL®, San Ramon, Calif., U.S.A.) using GENFRA™ (Accelrys) were transformed and a library of 343, 802 structures was obtained suitable for the virtual screening software LUDI (as opposed to Dock used by Orita et al. (Orita et al., 2001)). The first three energy functions were used and a manual consensus score ranked the lists. The top 100 hits were ranked and of these, 76 compounds were found to be commercially available and obtained through CHEMNAVIGATOR® (San Diego, Calif., U.S.A.; Walters and Murcko, 2002). Of the 76 compounds initially obtained, only 41 were found to be soluble in aqueous solutions at 100 μM concentrations. The 35 aqueous insoluble compounds can be further tested for their solubility and catalytic inhibitory activities at lower concentrations. Of the 41 compounds that were initially soluble, 9 were found to be inhibitory to the catalytic activity of purified, recombinant MIF (22.0% success rate (9/41) against purified protein compared to the <3% described in Orita (Orita et al., 2001)). When these compounds were tested against the catalytic activity contained in whole cell lysates to evaluate specificity in a cellular environment (not done in Orita's study), it was found that three compounds remained inhibitory. One was found to exhibit superior inhibitory activity against both MIF catalytic and biologic activities: 4-iodo-6-phenypyrimidine (see FIGS. 6 and 7).

Figure 8:
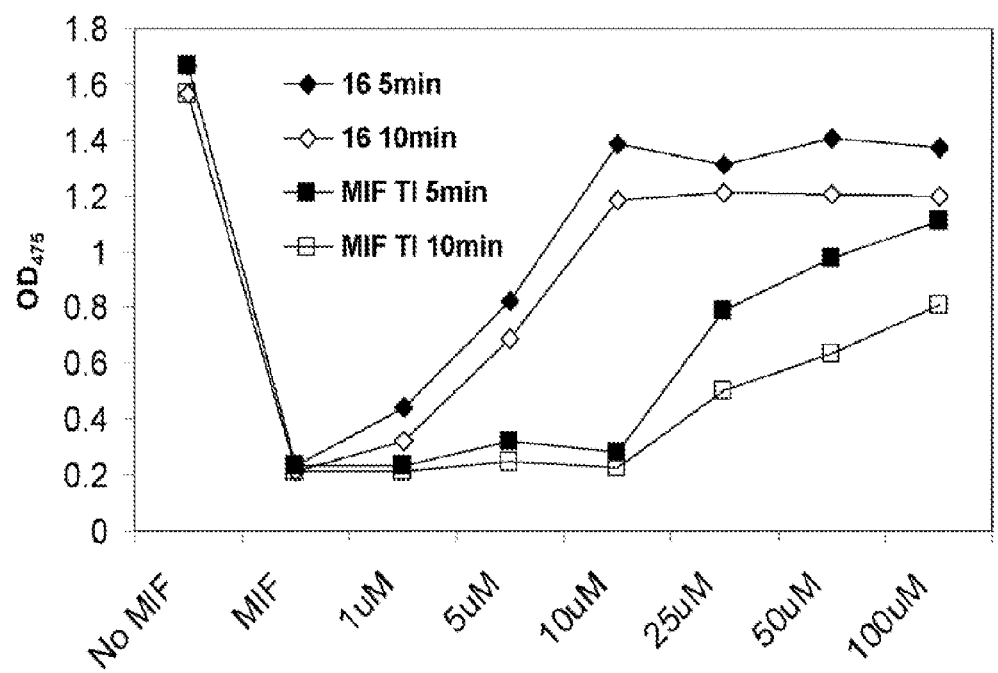
FIG. 8 is a graph showing the MIF inhibitor 4-iodo-6-phenylpyrimidine is a more potent MIF enzyme inhibitor than 3', 4',7-tryhydroxyisoflavone. 500 nM recombinant MIF (rMIF) was pre-mixed for either 5 (filled) or 10 (open) minutes with the indicated inhibitor concentrations followed by the addition of 2 mM final concentration of L-dopachrome methyl ester substrate. 5 minutes later OD 475 was measured spectrophotometrically, with tautomerization leading to colorless substrate.

Orita and colleagues identified 524 potential inhibitors and tested them for MIF tautomerase inhibition. Of these they found that 14 had MIF enzyme inhibitory activities (hit rate ~2.67% —compared to present hit rate of ~20%), with $K_i$ values reportedly ranging between 0.038 to 7.4 μM. In order to further validate the present novel virtual screening approach and compounds identified using it, the identified compounds were tested against the most potent inhibitor identified in this earlier screen. This compound, 3', 4',7-tryhydroxyisoflavone (TI—reported $K_i$ of 38 nM), was obtained from two independent companies and compared to three of the presently-identified compounds. Surprisingly, while TI had been reported to have a $K_i$ of 38 nM, the assay results conducted by the present inventors and colleagues indicated that 3', 4',7-tryhydroxyisoflavone was several orders of magnitude weaker than claimed and exhibited similar inhibitory activities as two of the presently disclosed compounds. Furthermore, 4-iodo-6-phenylpyrimidine (also referred to in the Examples and figures as compound #16), was found to have an $IC_{50}$ that was 5x lower than that of 3', 4',7-tryhydroxyisoflavone (TI) (16~5 μM versus TI~25 μM) (FIG. 8). Of note, similar results were obtained from both commercial sources of 3', 4',7-tryhydroxyisoflavone. This finding suggests that the presently-identified MIF antagonist, 4-iodo-6-phenylpyrimidine is the most potent MIF inhibitor reported to date. It is believed that, combined with further data described herein, this validates the novel presently-disclosed virtual screening approach proposed to identify novel small molecule inhibitors of MIF.

Example 5

Figure 4:
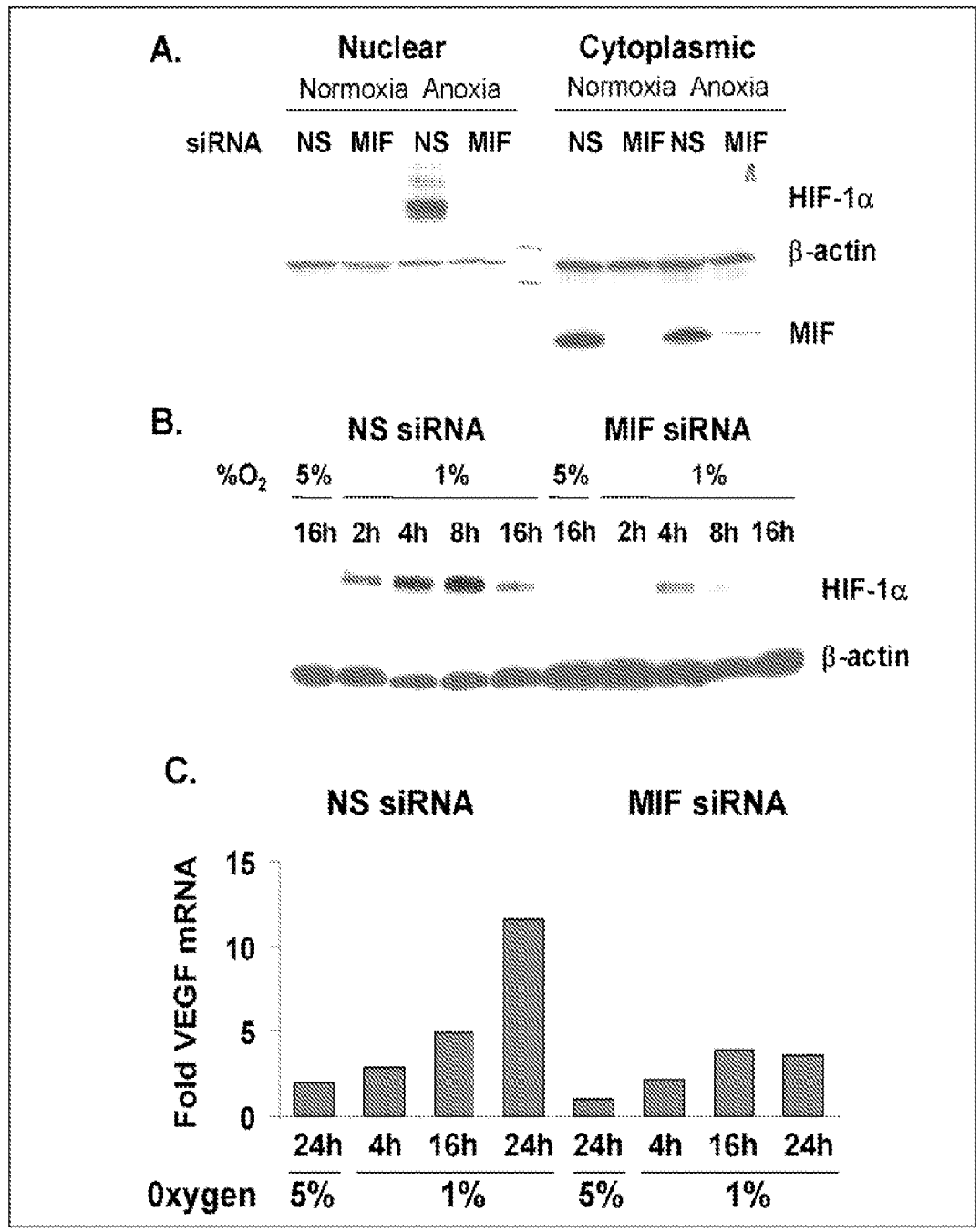
FIGS. 4A-4C show data demonstrating that loss of MIF results in de-stabilization of hypoxia-induced HIF-1α. Nuclear and cytosolic extracts from MIF-depleted cells were exposed to normoxia, anoxia (FIG. 4A) or hypoxia (FIG. 4B) and immunoblotted for HIF-1α.

Small Molecule MIF Catalytic Inhibitors Block HIF-1αStabilization in an MIF-Specific Manner As noted hereinabove, (see FIG. 4), it has been determined that MIF is necessary for hypoxia and prolyl hydroxylase inhibitor-induced HIF-1αstabilization and subsequent hypoxic adaptation of pancreatic adenocarcinoma cells. It was next tested whether MIF pharmacologic inhibitors were capable of recapitulating the destabilizing effects on HIF-1α we had observed using MIF siRNA (FIG. 4). In addition to testing the newly-determined MIF antagonist 4-iodo-6-phenylpyrimidine (also referred to as "compound #16"), the TI compound identified in the Orita screen (FIG. 8) was also tested. Inhibition of MIF by compound #16 completely inhibited HIF-1α stabilization induced by $CoCl_2$ (a prolyl hydroxylase inhibitor) in pancreatic carcinoma cells when used at very high concentrations (100 μM—FIG. 9A).

It was next tested whether the observed differences in the catalytic inhibitory activities between these two compounds was similarly observed in this biological assay of MIF inhibition. As shown in FIG. 9B, 4-iodo-6-phenylpyrimidine inhibited HIF-1α stabilization in a dose dependent manner and suppressed HIF-1α nearly 50% of control at 10 μM. In contrast, 3', 4',7-tryhydroxyisoflavone displayed no inhibitory activity at 10 μM and only slight inhibitory activity at 50 μM. Of note, this ~5 fold difference in biological inhibitory activity closely corresponds to the ~5 fold difference in enzymatic inhibitory activity that was observed when comparing these two compounds (FIG. 8). It is significant to note that similar inhibitory effects were observed on $CoCl_2$-induced VEGF expression and secretion (as measured by ELISA), with #16 suppressing greater than 80% of PHD inhibitor induced VEGF at 50 μM compared to a roughly 20% decrease in VEGF with TI. Intriguingly, ISO-1 was also able to inhibit HIF-1α stabilization induced by $CoCl_2$ but was only moderately effective at concentrations of 100 μM or higher, which correlate very closely with its enzyme inhibitory activity (FIG. 10).

Lastly, in order to verify that the effect of #16 on HIF-1α inhibition is through its inhibitory effects on MIF, MIF-containing cells and MIF-deficient cells were tested for inhibitory activity. As shown in FIG. 9C, #16 potently blocks HIF-1α stabilization in $MIF^{+/-}$ murine embryonic fibroblasts while $MIF^{-/-}$ fibroblasts were unaffected by the MIF inhibitor. Without wishing to be bound by theory, this finding can be significant for two reasons: 1) this demonstrates MIF specificity for compound #16 and, 2) this provides an additional and valuable screening tool to assess MIF specificity of congeners of #16 as well as other newly identified potent small molecule MIF inhibitors.

Combined, these data suggest the identification of a new class of indirect HIF-α inhibitors. Because of its central importance in conferring hypoxic adaptation and the resultant aggressive and metastatic phenotypes, there is a tremendous push right now to identify small molecule inhibitors of HIF-α. The present findings suggest that small molecule targeting of MIF represents a unique, indirect means of inhibiting this important transcription factor.

Example 6

Figure 9:
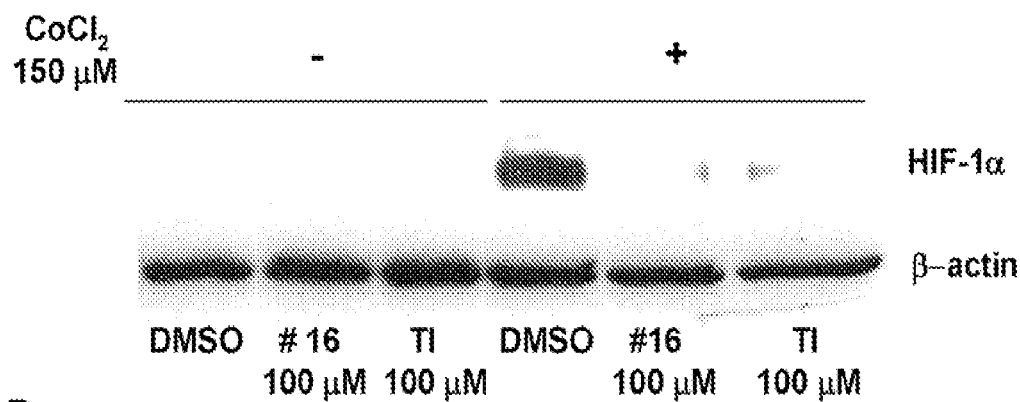
FIGS. 9A-9C are pictures of immunoblots showing MIF tautomerase inhibitors block HIF-1 stabilization in an MIF-specific manner. Cells were pretreated with or without DMSO or the indicated concentrations of the MIF antagonist 4-iodo-6-phenylpyrimidine (#16) or Orita compound 3', 4',7-Tryhydroxyisoflavone (TI) for 1 hour before challenging cells with CoCl2. After 5 hours, nuclear lysates were isolated and subjected to immunoblotting for HIF-1.
Figure 9:
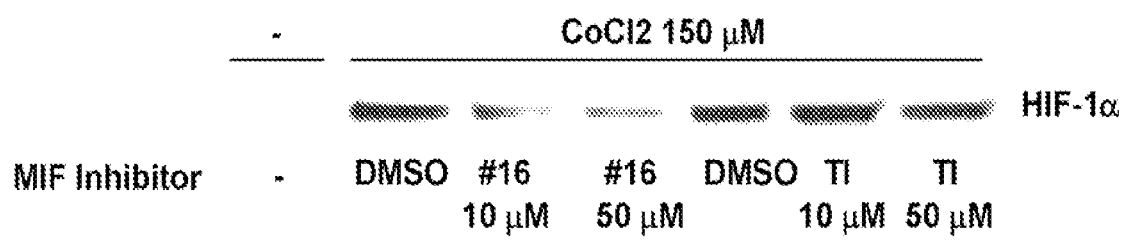
Figure 9:
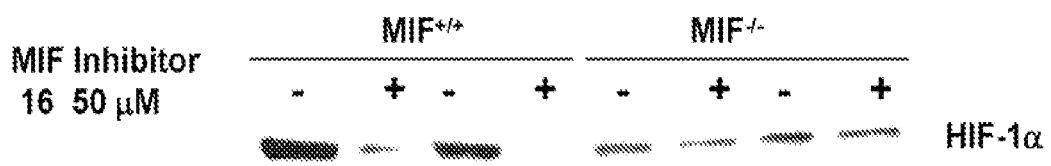
Figure 10:
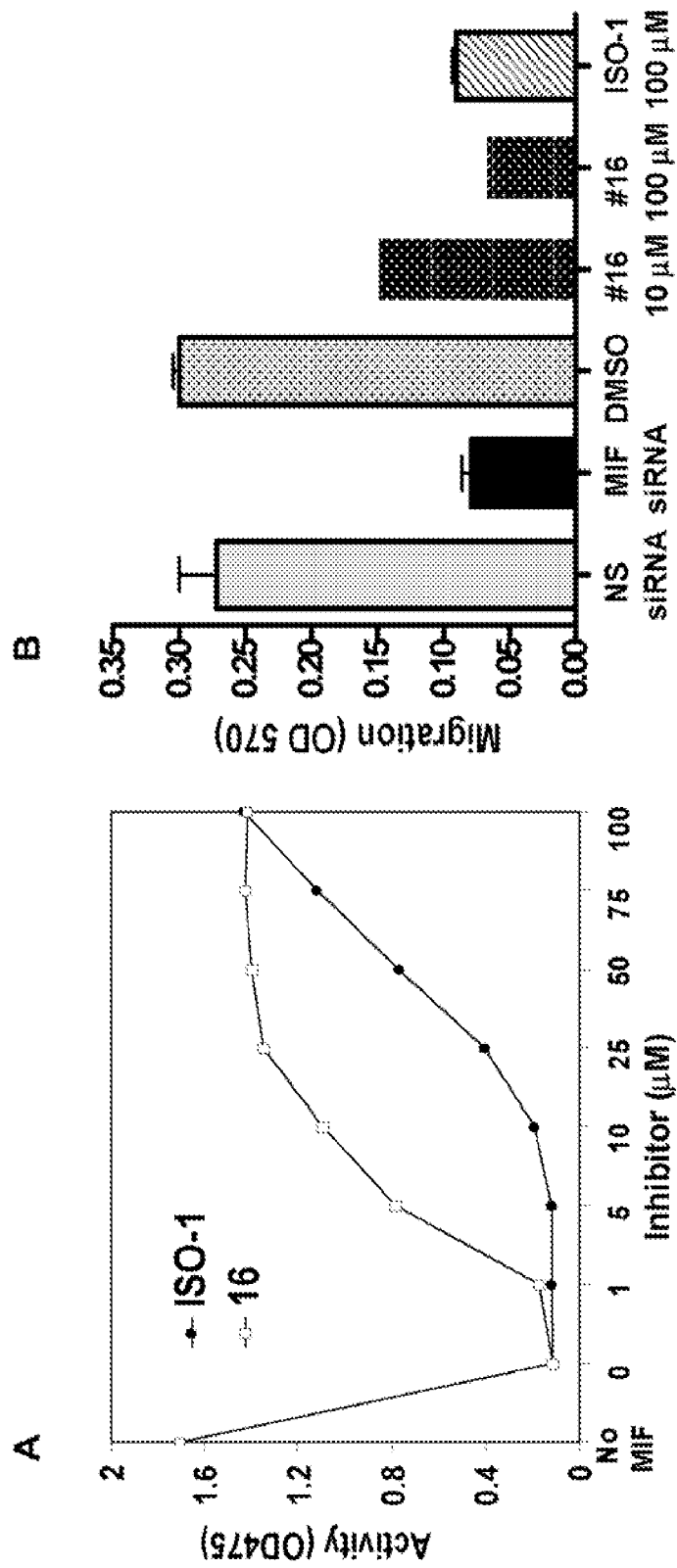
FIGS. 10A and 10B are graphs showing that the MIF inhibitor 4-iodo-6-phenylpyrimidine is more potent than ISO-1.

MIF Antagonists Inhibit MIF-Dependent Cell Migration and Anchorage-Independent Growth The above Examples demonstrate that the previously described prototype for catalytic MIF inhibitors (e.g., 3', 4',7-tryhydroxyisoflavone~FIGS. 8 and 9 is a less effective catalytic and biologic inhibitor of MIF's actions than the presently-identified MIF inhibitory compounds. The prototypical MIF biologic inhibitor (ISO-1) was next evaluated against the presently-identified MIF inhibitory compounds, and in particular, 4-iodo-6-phenypyrimidine. ISO-1 is a well-characterized inhibitor of both in vitro and in vivo biologic actions of MIF (Lubetsky et al., 2002; Nicoletti et al., 2005; Al Abed et al., 2005; Meyer-Siegler et al., 2006). Recent studies from the present inventors and colleagues (Rendon et al., 2006) and other laboratories (Ren et al., 2006; Sun et al., 2005; Ren et al., 2005; Meyer-Siegler et al., 2006) reveal that MIF is necessary for maximal tumor cell migration/invasion and ISO-1 inhibits MIF-dependent cell migration and anchorage-independent growth (Rendon et al., 2006; Meyer-Siegler et al., 2006). As such, 4-iodo-6-phenypyrimidine (also referred to herein as "compound #16") was tested against ISO-1 and determined relative inhibitory effects on both catalytic and biologic activities of MIF. As shown in FIG. 10, compound #16's $IC_{50}$ is 10× less than ISO-1 for both enzyme and migration inhibition (ISO-1 at 10 µM is completely inactive) indicating that this molecule is a significantly more potent and viable MIF antagonist than ISO-1. Importantly, these migration inhibition results are nearly identical when done in the same manner in MIA-PaCa-2 pancreatic adenocarcinoma cells.

Figure 11:
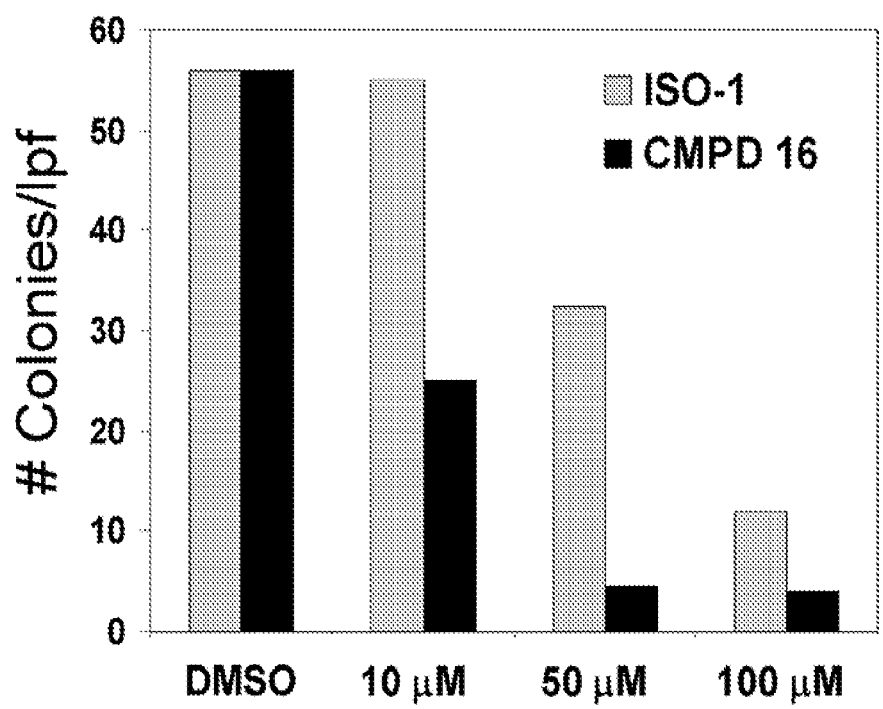
FIG. 11 is a graph showing inhibitors of MIF prevent anchorage-independent growth. 10$^5$ A549 human lung adenocarcinoma cells were plated in soft agar, containing vehicle (0.1% DMSO) or 10, 50 or 100 μM ISO-1 or 4-iodo-6-phenylpyrimidine (CMPD 16). 20 days later, colonies were stained and enumerated. Data are representative of two independent experiments.

The relative capabilities of ISO-1 and #16 to inhibit lung adenocarcinoma anchorage-independent growth were next tested and compared. As shown in FIG. 11, both ISO-1 and compound #16 inhibit A549 soft agar growth, but #16 was found to be between 5-10 fold more potent (similar to $IC_{50}$ data from FIG. 10) than ISO-1. Not only is this finding important because it validates the use of small molecule targeting of MIF in malignant disease intervention, but also because it identifies a novel, more potent MIF inhibitor than any other reported compound.

Figure 12:
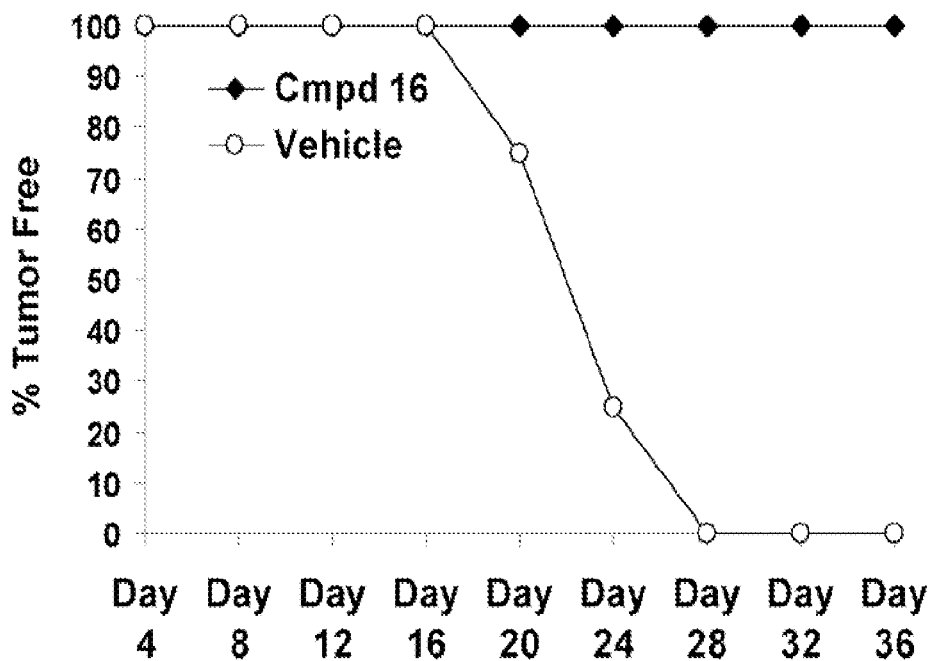
FIG. 12 is a graph showing Inhibition of NSCLC tumor growth by the MIF inhibitor 4-iodo-6-phenylpyrimidine. Balb/c (nu/nu) mice were injected with 1×106 A549 human lung adenocarcinoma cells subcutaneously (4 mice/group). Vehicle or 4-iodo-6-phenylpyrimidine (Cmpd 16; 2 mg) were injected intraperitoneally every day for the course of the study. Tumor growth was monitored by palpation every fourth day as indicated. Results are expressed as percent of tumor free mice/group.

In a study designed to evaluate the in vivo efficacy of anti-MIF compounds, 4-iodo-6-phenylpyrimidine (compound #16) was tested in a xenograft model of human non-small cell lung cancer (NSCLC) outgrowth. Because it was found that compound #16 inhibited anchorage-independence of A549 (FIG. 11) it was hypothesized that tumor outgrowth would be similarly inhibited. As shown in FIG. 12, while vehicle treated mice developed subcutaneous tumor lesions beginning at day 16, mice treated with Cmpd 16 remained tumor free. These data suggest that compound #16, and related compounds of Formula I disclosed herein, are deliverable and can in fact inhibit tumor outgrowth.

Figure 13:
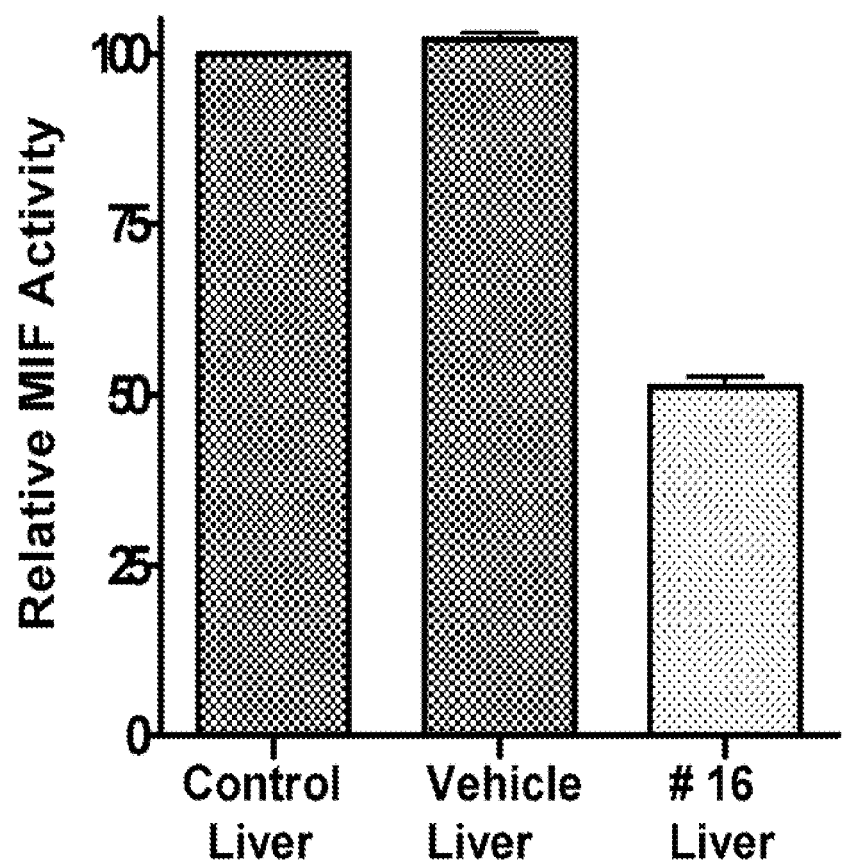
FIG. 13 is a graph showing the MIF inhibitor 4-iodo-6-phenyl pyrimidine inhibits MIF in vivo. C57Bl/6 mice were injected with corn oil or 1 mg 4-iodo-6-phenyl pyrimidine (# 16) suspended in corn oil for 6 hours before removal of the livers. After homogenizing tissue, 100 mg total liver protein was assessed for L-dopachrome methyl ester tautomerase activity.

A study to determine the MTD and in vivo inhibitory activity of compound #16 was also completed. Using 2 mice per group, it was found that daily injections (for 7 days) of 0.5, 1, 2 and 4 mg doses (25, 50, 100 and 200 mg/kg, respectively) of 4-iodo-6-phenylpyrmidine revealed no apparent toxicity. In vivo enzyme inhibition by compound #16 was next analyzed. A single bolus injection of 50 mg/kg of 4-iodo-6-phenylpyrimidine was found to inhibit endogenous liver MIF enzyme tautomerase activity at 6 hours post-injection by greater than 50% (FIG. 13). Combined, these data demonstrate that presently disclosed MIF antagonists, as exemplified by 4-iodo-6-phenylpyrmidine, are both safe and active in in vivo studies and are about ten times more effective than the prototypical MIF small compound inhibitor, ISO-1. Further, the discovery of the present MIF inhibitory compounds of Formula I disclosed herein by the present novel virtual screening and systematic testing methods validates the present approach and experimental design to identify further MIF small molecule inhibitors.

Example 7

MIF Inhibitors Block MIF/MIF Receptor Interactions

As previously noted, the ability of small molecule antagonists to block MIFs biological functions requires the blockade of MIF binding to its cell surface receptor (Meyer-Siegler et al., 2006). A high throughput assay has been designed to investigate inhibitors of MIF binding to its cell surface receptor, CD74 (Leng et al., 2003). The capture assay is based on the binding of a biotinylated human recombinant MIF (hrMIF) ligand to bind to the extracellular MIF binding domain of CD74 (see FIG. 14C).

To assess potential inhibitors of MIF/MIF receptor interaction, biotinylated MIF was co-incubate with MIF specific inhibitors or unlabeled MIF. In the case of unlabeled MIF, this also provides a simple experimental approach to measuring relative MIF receptor binding ability of site specific mutants that can be constructed for structure-function studies.

Figure 14:
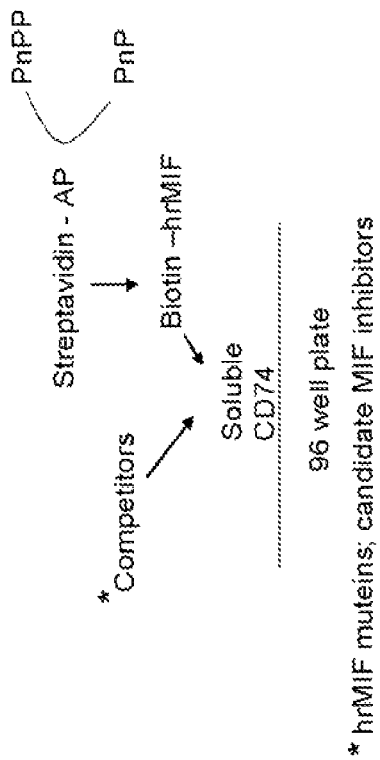
FIGS. 14A-14C are a schematic (FIG. 14C) of a MIF/MIF receptor capture assay and graphs of data collected from the assay (FIGS. 14A and 14B) that provides a tool for structure-function studies of MIF muteins and candidate inhibitors.
Figure 14:
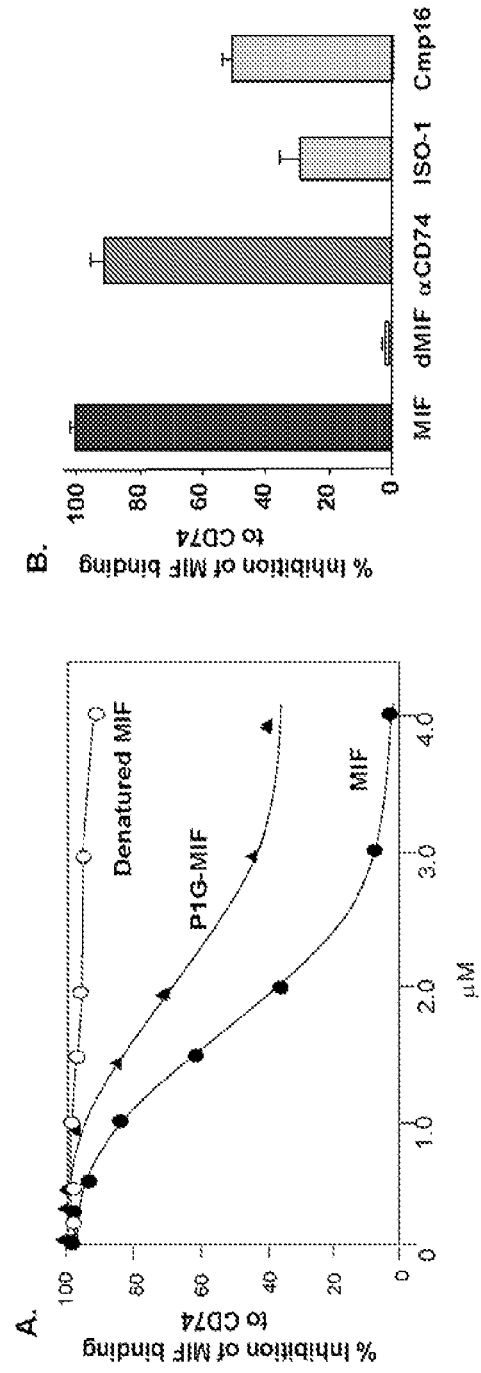

By way of example, FIGS. 14A and 14B show two capture assay experiments demonstrating: 1) partially defective CD74 binding by an MIF protein mutated at Pro-1 and which is known to be required for both enzymatic and biologic function (Swope et al., 1998) (FIG. 14A); and, 2) very efficient blocking of MIF/sCD74 by compounds 16 and ISO-1 (FIG. 14B). Note that for the experiment described in FIG. 14B, the maximal inhibition possible for this assay is 50% due to the use of only 0.1 µM MIF antagonist against 0.2 µM biotinylated MIF used. As such, compound #16 inhibits MIF receptor binding at the highest possible percentage (i.e. 50%). Note also the increased efficacy of compound #16 over ISO-1 in blocking MIF/MIF receptor interactions. This capture assay is clearly a very valuable tool with which to study structure-function relationships between enzyme and biologic activities. Moreover, binding studies testing mutant MIF proteins can reveal amino acid residues with which to modify for small molecule MIF targeting screens. It is expected that receptor binding data gleaned from candidate compound testing coupled with those from individual point muteins can enable one to modify and expand amino acid residue targets within the active site of MIF.

Discussion of Examples 1-7

All solid tumors require microenvironmental adaptation throughout tumorigenesis. One of the hallmarks of this adaptive response is the development of intratumoral hypoxia that stimulates HIF-directed expression of pro-tumorigenic/angiogenic genes. The present findings establish that one of these gene products, MIF, is elevated in pancreatic cancer patients and represents one component of a unique functional inter-relationship between the extracellular cytokine/growth factor MIF and the transcription factor, HIF-1α. This point is demonstrated by the present data showing that cells lacking MIF or those treated with small molecule MIF antagonists are refractory to hypoxia and PHD inhibitor-induced HIF-1α stabilization and subsequent transcription of metabolic and angiogenic gene products. Because HIF expression is described as contributing directly to tumor aggressiveness and cancers of the pancreas are reportedly very hypoxic (Koong et al., 2000b), it is likely that MIF functionally contributes to tumor maintenance, environmental adaptation and ultimately prognosis. Thus, the presently disclosed MIF antagonists represent a new class of indirect HIF-1α antagonists and anti-cancer agents.

Example 8

Identify Additional Amino Acids Necessary for MIF Receptor Binding/Catalytic Activity to Further Refine Computational Virtual Screens Against MIF Several MIF recombinant protein expression plasmids are constructed containing individual point mutations to assess their relative structure-function relationship to MIFs biologic (in vitro receptor binding) versus catalytic actions. To identify novel, more potent inhibitors of MIF, virtual screens can be carried out focusing on those amino acids found to be necessary for receptor binding and/or catalytic functions. Several virtual libraries consisting of over 18,000,000 compounds can be computationally screened.

Generation of site-specific mutations in human MIF. A re-investigation of the three dimensional structure of MIF reveals that there are several well conserved amino acid residues surrounding and within the substrate binding pocket of MIF that may either directly influence MIF/substrate interactions or could conceivable modify the binding pocket properties. Residues reported to be important for substrate binding to MIF include: Pro-1, Lys-32, Ile-64 from one MIF monomer and Tyr-95, Asn-97 from an adjacent one (Lubetsky et al., 1999). The present inventors and colleagues have identified numerous other residues from the crystal structure of the MIF/substrate binding pocket that are potentially important for docking or binding of the substrate/receptor. These include residues: Met-2, Pro-33, Tyr-36, His-62, Ser-63, Lys-66, Met-101, Val-106, Trp-108 and Phe-113. Interestingly, with the exception of Met-101, these residues are extremely well conserved throughout many species and, in some cases, between the distant MIF relative, D-dopachrome tautomerase (Swope et al., 1998).

All site specific mutations can be made by the use of the QUICKCHANGE® Site-Directed Mutagenesis Kit (Stratagene, La Jolla, Calif., U.S.A.). Briefly, PCR primer pairs can be made containing the mutation(s) of interest and PCR amplification of pET11b/MIF prokaryotic expression plasmid (Bernhagen et al., 1994) performed as described by the manufacturer. All residues targeted for mutation can replace the amino acid of interest with alanine and all mutants can be verified by sequencing.

MIF enzyme can be expressed, purified and refolded as described (Bernhagen et al., 1994) for each mutant. Relative enzymatic activities can be assessed as described immediately below and CD74 binding studies can be determined as described hereinbelow. These mutational data can be used to identify critical residues of MIF that will be targeted in lead anti-MIF small molecule antagonists. This information can further enable the refinement of the virtual screen as well as indicate additional sites that chemical synthesis should target by building off the existing compounds to include interactions with these residues.

Dopachrome tautomerase assay. Prior to testing candidate compounds in MIF specific bioassays, all identified antagonists can be screened for their respective abilities to inhibit MIF-dependent catalytic activity in the dopachrome tautomerase assay. MIF catalysis and inhibitory studies can be performed as described (Lubetsky et al., 2002). Briefly, L-Dopachrome methyl ester can be prepared at 2.4 mM through oxidation of L-3,4-dihydroxyphenylalanine methyl ester (Sigma, St. Louis, Mo.) with sodium periodate as previously described (Dios et al., 2002). Activity can be determined at room temperature by adding dopachrome methyl ester (0.3 ml) to a cuvette containing 500 nM rMIF (Bernhagen et al., 1994) in 50 mM potassium phosphate buffer, pH 6, 0.5 mM EDTA and 5 minutes later measuring the decrease in absorbance at 475 nm spectrophotometrically. All mutant MIF enzymes purified as described above can be tested against the relative activity of wildtype MIF enzyme using this method. Additionally, candidate inhibitors identified in the last section of the present Example can be dissolved in DMSO at various concentrations and added to the cuvette (final concentration of DMSO will be no more than 0.1%) with the MIF 1 minute prior to the addition of the dopachrome substrate.

CD74 capture assay. Soluble CD74 protein ($sCD74^{73-232}$) can be expressed and purified as described previously (Leng et al., 2003). Briefly, the cDNA comprising coding region of A.A. 73-232 can be PCR amplified and ligated into the pCR T7/CT TOPO F E. coli expression vector (Invitrogen, Carlsbad, Calif., U.S.A.). Recombinant sCD74 can be expressed in E. coli BL21 (DE3)pLysS under IPTG induction. The sCD74 protein can be purified from bacterial lysates by Ni-NTA affinity chromatography. Biotinylation of hrMIF can be performed according to manufacturer's instructions (Biotin Labeling Kit; Roche Molecular Biochemicals, Indianapolis, Ind., U.S.A.).

96 well plates can be coated with 60 µl/well of purified, soluble CD74 ($CD74^{73-232}$) at 0.1 mg/ml and incubated at 4° C. overnight. Plates can be washed with T-TBS and then incubated in SUPERBLOCK® (Pierce, Rockford, Ill., U.S.A.) at 4° C. overnight. After removal of blocking buffer, various concentrations of anti-CD74, denatured MIF, MIF, or mutant MIFs can be incubated for 30 mins at room temperature. 0.2 µM of biotin-MIF is then added directly to the plate and incubated at 4° C. overnight. For inhibitor assays, various concentrations of the compound can be pre-incubated with 0.2 µM biotin-MIF for 30 mins at room temperature in the dark before adding to plates and incubating overnight. After washing the plate 4 times with T-TBS, Streptavidin-AP (R & D Systems, Minneapolis, Minn., U.S.A.) is added to wells and incubated for an additional 1 hour at room temperature in the dark. After washing, 60 µl/well of PNPP (Sigma) is added and allowed to develop in the dark until being read at 405 nm.

Virtual screening against MIFs catalytic active site. Computational methods can be utilized to screen up to 18 million potential small molecule inhibitors of MIF. The strategy starts with the dictate that target binding site is the methionine (A2) at the base of the MIF binding pocket, as disclosed hereinabove. This target residue is unique from previously described virtual screens (Orita et al., 2001) and the data presented herein indicates that additional compounds can be discovered using this novel approach. In addition to targeting Met A2, the results of mutation data can be incorporated to include those regions found to be important in the MIF/MIF receptor interactions and/or those found to be necessary for catalytic function. A variety of virtual screening software with different scoring algorithms can be run to arrive at a consensus score for identifying lead compounds to test against both the catalytic and biologic activities of MIF. The latest versions of DOCK (Ewing et al., 2001), FlexX (Rarey et al., 1996) and CSCORE™ (Tripos, St. Louis, Mo., U.S.A.) can be used for prescreening the larger databases to derive a smaller binding database that can be examined using more flexible protocols with DOCK 6.1 (allows flexible receptor), Autodock (Goodsell et al., 1996), Surflex (Jain, 2003), and Molegro (Thomsen & Christensen, 2006). An advantage of using more than one method and scoring technique is that there is no universal way that this is transferable to any system. When combined, this also increases the enrichment of the "hits" and reduces false positives.

Small molecule databases that can be searched and contain compounds that are commercially obtainable are; the NCl diversity set containing 1,990 small molecules with Sybyl generated Gasteiger charges, ZINC library that currently contains over 4,600,000 small molecules with the more accurate AMSOL calculated partial charges (this is an alternative to the ACD library with a greater number of molecules that have been filtered for size, logP, number of H-bond acceptor and donors in accordance to a relaxed Lipinski's rule of (Walters et al., 1999; Walters and Murcko, 2002; Lipinski, 2000) and Chemnavigator (Walters and Murcko, 2002) iResearch library with over 14,000,000 unique, commercially available structures. The iResearch library can be checked for overlap with the ZINC library and the unique structures can form a new library. For the iResearch 2D database CONCORD can be used generate 3D conformations.

Figure 7:
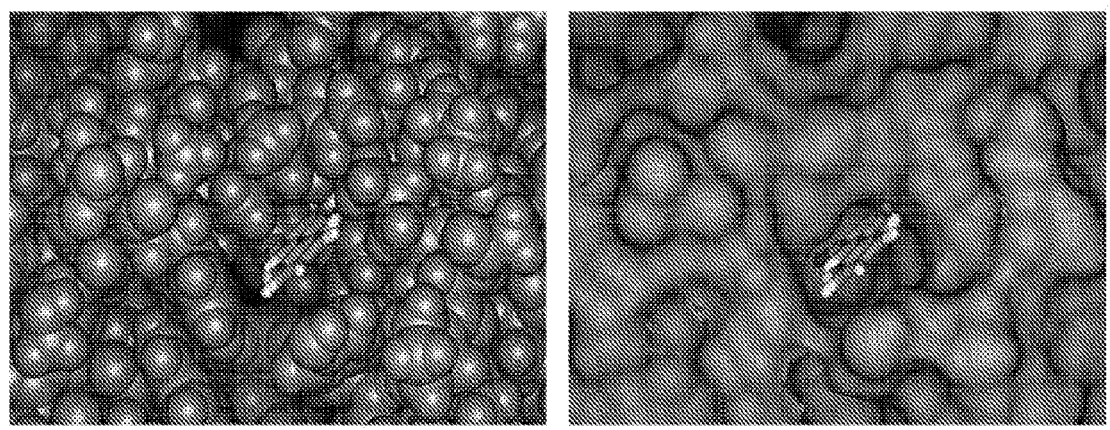
FIG. 7 is a computational model showing molecular interactions between an exemplary MIF inhibitor, 4-iodo-6-phenylpyrimidine, and MIF. Note the iodo group positioned at the base of the hydrophobic binding pocket at Met A2.

The data shown in FIG. 7 was generated using a rigid docking procedure with Ludi (Accelrys) software and the ACD library (converted using Corina and Genfra). However, Ludi may not perform as well as the docking software mentioned above, and is limited with respect to ligand flexibility and partial charges. An initial DOCK screen can use a grid spacing of 0.3 Å, contact cutoff of 4.5 Å, and an energy cutoff at 10 Å. AMBER (Cornell et al., 1995) charges can be used for grid generation for MIF target binding pocket. A rigid ligand docking can then be performed and combined with the contact score, chemical score and energy scores for the top 10,000 molecules. These can be subsequently used for fully flexible docking. A similar approach can be used with the other virtual screening software. The protocols can be adapted depending on the results.

Example 9

Compound Optimization Through Virtual Combinatorial Library Screening and Receptor Binding Data Analyses This Example builds on identified and tested inhibitors of MIF, as well as unique templates identified using the methodology of targeted virtual screening outlined in Example 9. Both virtual combinatorial library screening and data analysis from receptor binding/catalytic activities of point mutants can be used to deduce compound optimization.

Virtual combinatorial library generation and screening. The Sybyl software LEGION™ (Thorpe et al., 1999) allows for reaction based generation of combinatorial libraries where known chemical synthetic reactions are used to generate libraries of synthetically obtainable compounds. This enhances the possibility of designing a molecule that can actually be made as lists of reagents and reactions are generated for each new compound. Alternatively, LEGION™ can be used in a product-based manner that makes systematic changes to user defined sites of the core molecule. These libraries can then be more thoroughly evaluated using flexible docking software to allow for conformational flexibility of the ligand and receptor in the MIF binding pocket. This process can also be used for any new biologically active compounds that are found in Example 8. Should these procedures not result in new analogs that are more active, the alternative in silico combinatorial generation program COMBILIBMAKER™ (Cramer et al., 1998; Pearlman and Smith, 1999), which uses a library of side chains attached at user specified positions, can be used. The MIF mutation data from Example 8 can be used to direct the region of the template to "grow" the molecule to cover residue side chains important for the MIF/MIF receptor interaction and/or catalytic activity.

Figure 15:
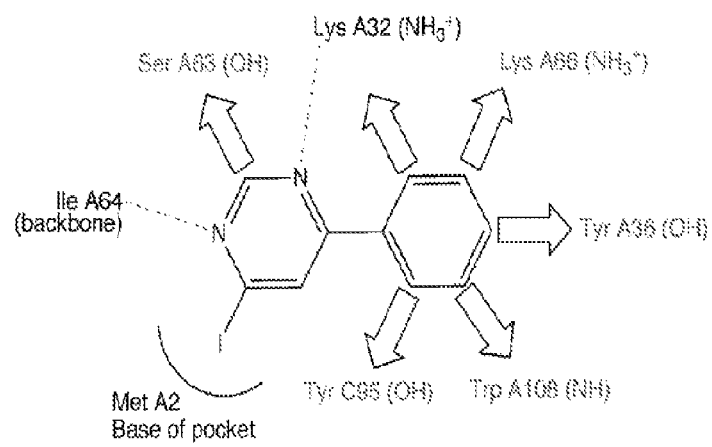
FIG. 15 is a schematic drawing showing interactions between MIF inhibitor 4-iodo-6-phenylpyrimidine and MIF.
Figure 16:
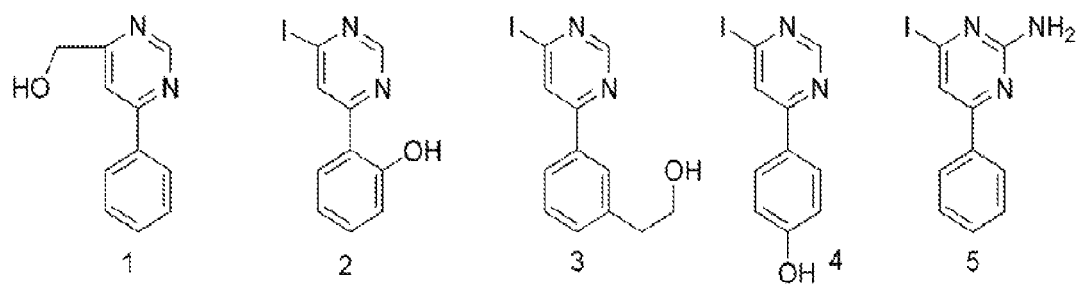
FIG. 16 is a schematic drawing of MIF inhibitor compound candidates derived from 4-iodo-6-phenylpyrimidine.

Compound optimization and synthetic scheme. 4-iodo-6-phenylpyrimidine and related compounds is unique among other ligands for MIF as, and without wishing to be bound by theory, it is the iodo group that is anchored in the base of the MIF binding at the Met A2 position (FIG. 15). The pyrimidine ring forms two hydrogen bonds, N3 to Ile A64 (backbone interaction) and N1 to side chain of Lys A32. The phenyl group gives additional stabilization by stacking on Tyr A36. The chemical optimization has several possibilities (FIG. 16): 1) modifying the iodo group to form a hydrogen bond to Met A2 (replacing I with a $CH_2OH$), 2) introducing an hydroxyl group at position 2 on the phenyl ring would hydrogen bond to N1 position of the pyrimidine as well as increase the electrostatic interaction (O—$NH_3$) with the side chain of Lys A32, 3) substitution at the 3 position of the phenyl group with a $CH_2CH_2OH$ would enable an interaction with the side chain of Lys A66, 4) substitution at the 4 position of the phenyl group with either a H-bond acceptor or donor to increase interaction with the OH of Tyr A36, 5) substitution at the 5 position of the phenyl group with a H-bond acceptor to enable an interaction with Trp A108 (NH), 6) substitution at the 5 and 6 positions of the phenyl group with a H-bond acceptor or donor to enable an interaction with Tyr C95 (OH), 7) substitution at the C2 position of the pyrimidine ring with a H-bond acceptor or donor to enable an interaction with Ser A63 (FIG. 15). Mutational data from Example 8 can provide important clues as to which residues to target and can therefore play an important role in determining which derivatives may be desirable to make and test.

A synthetic scheme is described for derivatization of MIF inhibitor compound, 4-iodo-6-phenylpyrimidine (Scheme 1). This scheme is meant to serve as a generalized template for synthetic studies for additional compounds identified from the virtual screening strategy described in Example 8. The stereo-electronic space can first be mapped around a lead compound. Accordingly, a synthetic sequence has been designed that utilizes a minimum number of steps, from readily available commercial starting materials and reagents. An added advantage of this synthetic plan is that the order can be modified in which substituents are incorporated on either one of the rings. In addition, if needed one can be able to functionalize the substituents (e.g., oxidation of alcohol, or substitution reactions to name a few). The synthesis of 1 can be done in one single step (Sakamoto et al., 1980) from a commercially available starting material 6, which in itself is an attractive candidate for testing (eq 1).

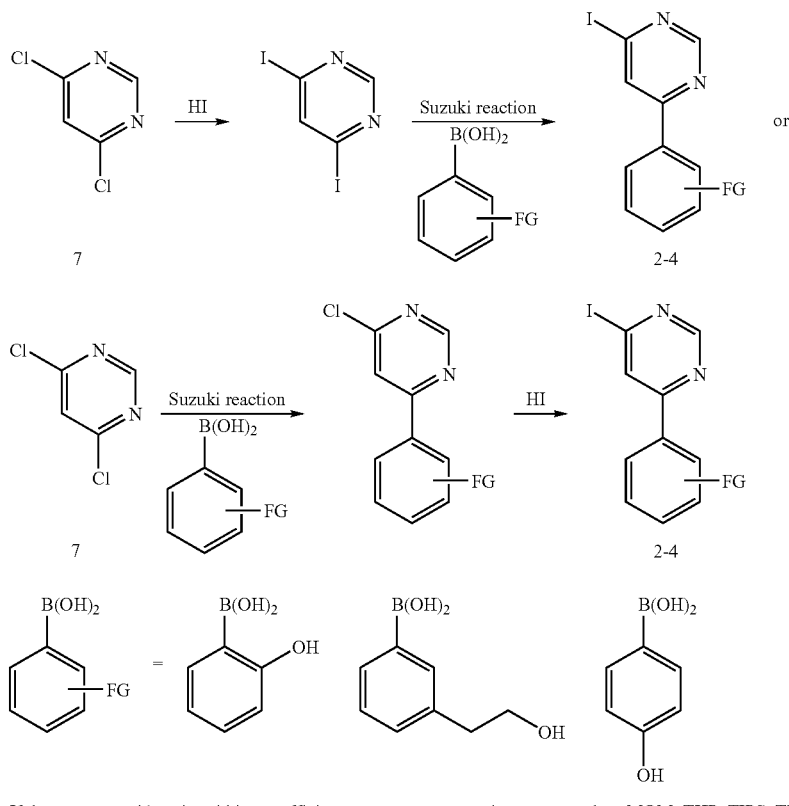

The synthesis of the alcohol derivatives 2-4 can be accomplished using a common sequence (Scheme 1) that employs a Suzuki coupling either in the first or the second step in this two-step sequence (Gong and Pauls, 2000; Wang et al., 2005; Saygili et al., 2004). An added advantage of this synthesis is that the boronic acids are commercially available and, if the hydroxy groups cause some difficulties, they can be easily protected with a variety of protecting agents, as show in the scheme. The synthesis of 5 is based on published procedures (Sawayama et al., 1977) and is shown in eq 2.

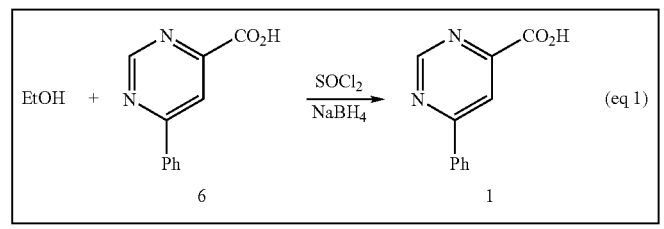

-continued

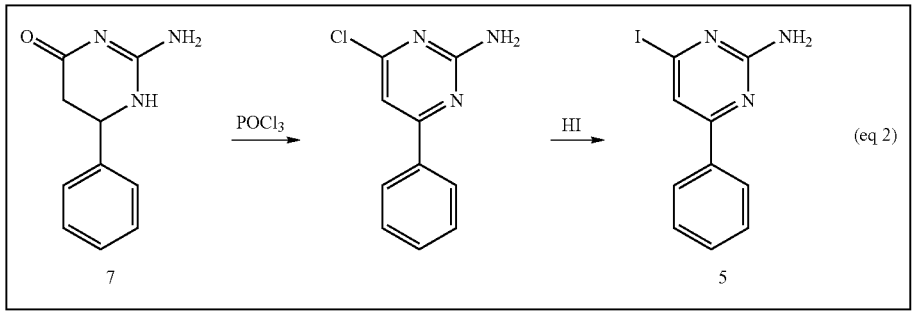

(eq 2)

By initially using the compound 4-iodo-6-phenylpyrimidine as a core structure and following the representative synthetic scheme illustrated above (Scheme 1), additional potent analogs of this MIF antagonist can be identified. Moreover, the virtual screening studies described in Example 8 can produce additional molecules of interest that can be available for analysis using the Sybyl software-generated combinatorial libraries followed by synthesis of lead derivatives. The extensive mutational analyses of MIF-dependent receptor binding/catalytic studies can reveal several amino acid residues that can be more appropriately targeted using novel substituent groups or expansion of/on the core structures disclosed herein.

Example 10

Screening and Assessment of Catalytic and Biologic Inhibitory Activities of Identified MIF Antagonists In addition to testing for inhibition of MIF-dependent catalysis and receptor binding described in Example 8, all candidate MIF inhibitory compounds can be tested in two independent in vitro MIF bio-assays. All lead derivative anti-MIF compounds as well as newly identified molecules can initially be tested for both catalytic and receptor binding inhibitory activities (see Example 8). Following the testing of these compounds for catalytic/receptor binding blocking activities, inhibitory effects on HIF stabilization and cell migration can then be assessed for all compounds regardless of enzymatic or receptor binding inhibition.

The requirements for MIF binding to CD74 can be tested in an HIF-1α stabilization assay. A prior study has shown that CD74 is, in fact, required for prostate cancer cell invasion and anchorage-independence and is likewise necessary for the ability of ISO-1 to block these effects (Meyer-Siegler et al., 2006). As shown in FIG. 9, MIF$^{-/-}$ cells are similar in phenotype to MIF siRNA transfected cells in that both cell types lacking MIF demonstrate significantly reduced PHD-inhibitor induced HIF-1α stabilization. CD74$^{-/-}$ fibroblasts can similarly be tested for their ability to stabilize HIF-1α induced by hypoxia or PHD inhibitors. In addition, candidate compounds found to be inhibitory in bioassays can be tested for specificity in both MIF$^{-/-}$ and CD74$^{-/-}$ mouse embryonic fibroblasts.

Screening of HIF-1α de-stabilization by candidate MIF inhibitors. The presently disclosed discovery that MIF plays a central role in HIF stability was from studies done in pancreatic adenocarcinoma cell lines. These studies further show that MIA-PaCa-2 pancreatic adenocarcinoma cells are very sensitive to MIF inhibitor-mediated HIF de-stabilization (FIGS. 9A and 9B). This cell line can be utilized for large scale testing of candidate MIF antagonists. In order to scale up this in vitro screen, a DuoSet ELISA-based assay to detect total HIF-1α in human cell lysates can be utilized (R & D Systems). The initial studies demonstrate that both MIF siRNA and MIF antagonist compound #16 (50 µM) inhibit CoCl$_2$-induced HIF stabilization ~75-90% that of control as assessed by this HIF-1α ELISA. MIA-Paca-2 cells can be plated at 5×10$^5$ cells/well in 24 well plates for 16 hours. Media can be replaced with fresh media containing 0.1% DMSO (− control), 50 µM #16 (+ control) and 5, 50 µM concentrations of test inhibitor, all in duplicate wells. After 1 hour, cells can be challenged with 150 µM CoCl$_2$ for an additional 6 hours. After rinsing the cells twice with PBS, supplied kit lysis buffer can be used to lyse the cells following manufacturer's directions. Prior coating and blocking of HIF-1α capture antibody can be performed according to instructions and diluted cell lysates can be assayed on the HIF-1α ELISA plates.

Those compounds demonstrating activities against HIF-1α accumulation can be tested more extensively and at a broader range of concentrations. Specifically, 10 fold increment doses can be tested ranging between 5 nM to 50 µM. Lead MIF inhibitory compounds can be further confirmed by evaluating inhibitory activities against hypoxia-induced (as opposed to PHD-inhibitor induced) HIF-1α. Additionally, compounds can be tested against hypoxia-induced VEGF expression by ELISA and GLUT-1 expression levels by western blotting.

Human pancreatic adenocarcinoma cell migration. It may be desirable to determine whether MIF-receptor binding is required for all of the inhibitory effects of MIF inhibitors. Meyer-Siegler et al. teaches that tumor cell migration and anchorage-independence require CD74 (Meyer-Siegler et al., 2006), but are less certain of a requirement for CD74 in MIF-dependent HIF stabilization. As such, all candidate anti-MIF compounds can be tested for inhibition of HIF stabilization and cell migration in human pancreatic adenocarcinoma cell lines to determine if there are correlative inhibitory activities in both assays and whether this correlates with MIF receptor binding and/or catalytic activity.

Briefly, 2×10$^5$ M IA-PaCa-2 human pancreatic adenocarcinoma cells can be resuspended in 0.3 mls of migration media (DMEM, 0.5% BSA) and allowed to incubate for 30 minutes in the presence of vehicle (0.1% Me$_2$SO), 5 µM or 50 µM candidate inhibitor. Collagen-coated (10 µg/ml in PBS-overnight) transwell chambers can be placed in 0.4 mls migration media and cells can be placed in the upper chamber. 16 hours later cells from upper chamber can be swabbed out and the membrane bottoms can be stained with crystal violet and solubilized with isopropanol/acetic acid followed by reading spectrophotometrically at OD 570. Those compounds exhibiting inhibitory effects on cell migration can be further tested at a broader range of concentrations (e.g., 5 nM to 50 µM) and $IC_{50}$ concentrations can be determined.

MIF receptor (CD74) requirements for HIF-1α stabilization and specificity of lead MIF inhibitors. To determine whether CD74 is necessary for MIF-dependent HIF stabilization wildtype (C57Bl/6) and CD74$^{-/-}$ (C57Bl/6) MEFs can be plated at nearly confluent conditions in duplicate in 24 well plates for 16 hours. In parallel, MIF$^{-/-}$ mouse fibroblasts (C57Bl/6) can be plated in duplicate at equal density. After 16 hours, cells can be challenged with either hypoxia (1% $O_2$) or PHD inhibitors for an additional 6 hours and cell lysates can be examined for relative HIF-1α stabilization by the total HIF-1α ELISA described hereinabove in the present Example. HIF concentrations (extrapolated from internal ELISA standard curves) can be evaluated to determine whether HIF stabilization induced by hypoxia or $CoCl_2$ is defective in CD74-deficient cells similar to the defect observed in MIF-deficient cells (FIG. 9).

In order to test the specificity of lead anti-MIF compounds, wildtype, MIF$^{-/-}$ and CD74$^{-/-}$ fibroblasts (all C57Bl/6) plated as above can be treated with previously determined HIF effective inhibitory doses for 1 hour followed by challenge with $CoCl_2$ for 6 hours. HIF-1α protein levels can then be determined by ELISA and relative decreases in wildtype MEFs can be compared to any decrease observed in MIF$^{-/-}$ and CD74$^{-/-}$ cells.

Lastly, parallel in vitro cytotoxicity studies can be performed alongside these experiments when and if it is suspected that there is any evidence of toxicity. Briefly, cells can be treated with vehicle (DMSO) or candidate compounds at concentrations ranging from 1 µM to 100 µM for 24 hours. For these studies a method of tetrazolium reduction known as ALAMAR BLUE™ (Serotec Limited, Oxford, United Kingdom) can be used. ALAMAR BLUE™ reagent can be added at a 10% solution to cells for 4 hours and then read on a fluorescent plate reader at wavelengths of 530 nm excitation and 590 nm emission. Toxicity can be assessed by dividing the fluorescence value from vehicle treated wells from those treated with individual drugs.

Example 11

Identified MIF Antagonist Testing to Determine Capability to Alter Pancreatic Tumor Growth and Pathology in a HIF-1α-Dependent Manner Tumor growth and associated hypoxic adaptation of transplanted pancreatic carcinoma xenografts in mice treated with lead anti-MIF compounds can be evaluated. Immunohistochemical analyses of HIF-1α and HIF-1α target genes (CA9, GLUT-1) can be evaluated along with various histological biomarkers such as angiogenesis, hypoxia, apoptosis and necrosis. Control pancreatic carcinoma cell lines expressing constitutive MIF siRNA or a dominant interfering mutant of HIF-1α can be tested both with and without inhibitor treatment to determine MIF and HIF specificity.

Determine tumor growth properties of human pancreatic xenografts in mice treated with lead MIF antagonists. The capacity of a CD74-positive human pancreatic adenocarcinoma cell line to develop into solid tumors in the presence of: 1) anti-MIF inhibitor 4-iodo-6-phenylpyrmidine; 2) congeners of 4-iodo-6-phenylpyrimidine; and, 3) lead and optimized lead candidate compounds identified from Examples 8-10 can be examined. $2 \times 10^6$ MIA-PaCa-2 cells can be injected subcutaneously into nude Balb/c (nu/nu) female mouse flanks. One implant can be performed per mouse and each experiment can consist of 10 mice/group (to be repeated once for a total of 20 mice/group). Control mice can be injected with corn oil alone while test mice can be injected with the anti-MIF compound in question (initial compound concentration=50 mg/kg; i.p. every 24 hours; diluted in corn oil). To obtain tumor growth curves, three mutually orthogonal diameters of tumors can be measured every day using Vernier calipers and mass can be determined using the following formula (Taetle et al., 1987): mass (mg)=(width, m)$^2$× (length, m)/2. Measured masses can be plotted as the mean relative treatment group tumor volume±SEM. After control tumors reach no more than 10% of total body mass (~2 gm), the mice can be euthanized and a small subset from each group can be sacrificed by cervical dislocation for hypoxia and hypoxia marker determination, IHC and vascularity indices as described in the section immediately below.

Compounds found to be most inhibitory as well as specific for MIF to tumor outgrowth in the pancreatic tumor xenograft model can then be tested in models of established tumors. Briefly, mice can be implanted subcutaneously with $2 \times 10^6$ MIA-PaCa-2 cells and Vernier calipers can be used to measure the mass as described hereinabove. Once the tumors reach 200 mg, mice can be separated into groups of 10 with equal tumor size representation of tumors in each group. Control mice can be injected with corn oil alone while test mice can be injected with the test compound (50 mg/kg; i.p. every 24 hours; diluted in corn oil). Tumor growth curves can be established from the outset of the implantation as described above. After control tumors reach 10% of total body mass (~2 gm), the mice can be euthanized and a small subset from each group can be sacrificed by cervical dislocation for hypoxia and hypoxia marker determination, IHC and vascularity indices as described in the section immediately below. Those compounds that are found to have maximal activity (when compared to MIF-deficient MIA-PaCa-2 cells) in these assays can be used for dose response determination for tumor growth inhibition as well as maximal tolerated dose testing.

Determining hypoxic characteristics, markers and vascularity of human pancreatic xenografts in mice treated with MIF antagonists. For initial testing with 4-iodo-6-phenylpyrimidine as well as other lead and/or congeneric compounds, tumor hypoxic markers and tumor-associated angiogenesis can be evaluated. Briefly, when tumor burden has been established mice can be sacrificed by cervical dislocation because of the confounding effects of anesthesia on hypoxia. Just prior to sacrificing the mice, HYPOXYPROBE-1™ (60 mg/kg; Southcot Corporation, Research triangle Park, North Carolina, U.S.A.) can be administered intravenously into a sub-group of mice. A small section of representative tumors from control and anti-MIF antagonist treated mice can be quick frozen in liquid nitrogen. After being weighed, the xenografts can be embedded in TISSUE-TEK™ (Sakura Finetechnical Co., Ltd., Tokyo, Japan) and stored at −70° C. until analysis. Serial sections can be cut from each embedded specimen. One section of each specimen can be stained with H&E. Additionally, another serial section can undergo in situ TUNEL assay using an apoptosis in situ detection kit (Wako Pure Chemical Industries, Ltd., Osaka, Japan) according to the manufacturer's protocol. Serial sections will also be examined for blood vessel content and hypoxia by anti-factor VIII (anti-mouse) and anti-pimonidazole staining, respectively. Other serial sections can be examined by IHC for HIF-1α, HIF-2α, CA9 and GLUT-1 (HIF-target genes). Correlations between hypoxic regions, vascularity and apoptosis can be evaluated in relation to the tumors from control mice.

Testing MIF-deficient and dominant negative HIF-1α expressing pancreatic adenocarcinoma tumor outgrowth and sensitivity to anti-MIF compounds. Without wishing to be bound by theory, attenuating effects observed in pancreatic tumor outgrowth by MIF antagonists can potentially be due to the inhibition of MIF-dependent HIF-1α stabilization and the resultant loss of hypoxic adaptation and neoangiogenesis. To further test this possibility, the relative effects of potential antagonists can be tested against MIA-PaCa-2 cell lines deficient in MIF expression or expressing a dominant inhibitory mutant HIF-1α. Furthermore, the unchallenged comparison of control vs. MIF or HIF defective cell lines abilities' to develop into solid tumors can provide important insights into whether MIF predominantly affects tumor outgrowth through modulation of HIF-1α.

Figure 17:
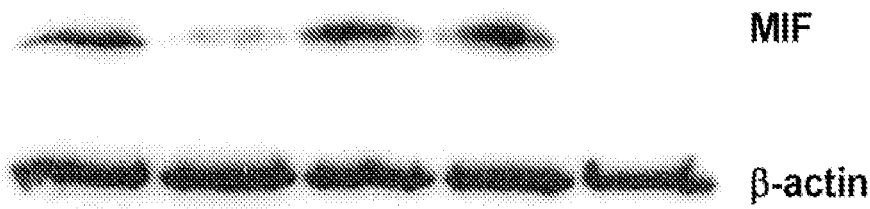
FIGS. 17A and 17B are photographs of blots showing stably-expressing MIF siRNA cell lines exhibit defective HIF expression. Scrambled siRNA (NS) or MIF-specific oligo containing pSuper (puro) plasmids were stably transfected into MIA-PaCa-2 cells and selected with puromycin. Four representative MIF siRNA clones were compared to an NS oligo expressing stable cell lines and immunoblotted for MIF (FIG. 17A). NS, clone 7 and clone 2 were treated with and without 150 μM CoCl2 for 6 hours and HIF-1α was assessed by western blot (FIG. 17B).
Figure 17:
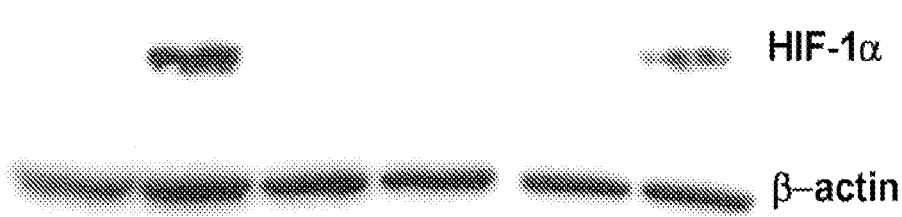

The dominant negative HIF-1α (d/n HIF-1α) mutant comprises the DNA-binding and dimerization domains but lacks any transactivation or $O_2$-regulatory domains (Forsythe et al., 1996). Dominant negative HIF-1α-expressing cell lines can be generated by retrovirally infecting MIA-PaCa-2 cells with retroviral supernatants made by transiently transfecting the Phoenix packaging cell line with pLXSN-HA-dnHIF-1α. The MIF-deficient cell line was recently developed by stably transfecting in an MIF specific MIF siRNA (FIGS. 17A and 17B). Briefly, $2 \times 10^6$ control, MIF-deficient (clone 7—FIGS. 17A and 17B) or d/n HIF-1α expressing cells can be injected subcutaneously into groups of 10 nude Balb/c (nu/nu) female mice (20 gms). For initial experiments, tumor outgrowth curves for each group can be assessed by mass determination as hereinabove. For lead compound studies groups of 20 mice can be injected with control, MIF-deficient (clone 7—FIG. 17) or d/n HIF-1α expressing cells. ½ of each group (10 mice) can be injected with corn oil alone while the other ½ can be injected with the lead compound in question (50 mg/kg; i.p. every 24 hours; diluted in corn oil). Tumor masses can be measured every 24 hours by Vernier calipers as described in the section above. After control tumors reach 10% of total body mass (~2 gm), the mice can be euthanized and a small subset from each group can be sacrificed by cervical dislocation for hypoxia and hypoxia marker determination, IHC and vascularity indices as described in the section above.

Maximal tolerated dosing of MIF antagonists in vivo. Because of the variability in drug sensitivities among individuals, it can be desirable to have an idea of what the maximal tolerated doses and therapeutic windows are for prospective clinical pharmaceuticals. Tests on promising anti-MIF lead compounds can be performed to determine their relative toxicities by performing a maximal tolerated dose (MTD) study. Having established that 50 mg/kg is tolerated, it can next be determined whether increasing doses are similarly tolerated starting first with 100 mg/kg and then proceeding stepwise with: 200, 300, 400 and finally 500 mg/kg doses in small groups of mice (e.g., 5 mice/group). During daily intraperitoneal injections of compound for 7 days, mice can be closely monitored for pain or discomfort up to 4 days after the last injection.

In summary, the soluble cytokine/growth factor, Macrophage migration inhibitory factor (MIF) represents a uniquely powerful target for structure-based drug design. MIF contributes to the growth, motility and hypoxic adaptation of tumors and MIF inhibitory small molecules block all of these protumorigenic effects. These findings, coupled with the fact that mice deficient in MIF develop and grow normally, strongly suggest that the potent MIF antagonists disclosed herein represent a new generation of less toxic and more potent anti-cancer disease therapeutics than those currently in use.

It will be understood that various details of the presently disclosed subject matter can be changed without departing from the scope of the presently disclosed subject matter. Furthermore, the foregoing description is for the purpose of illustration only, and not for the purpose of limitation.

REFERENCES

Al Abed, Y., Dabideen, D., Aljabari, B., Valster, A., Messmer, D., Ochani, M., Tanovic, M., Ochani, K., Bacher, M., Nicoletti, F., Metz, C., Pavlov, V. A., Miller, E. J., and Tracey, K. J. (2005) J Biol Chem 280, 36541-36544.

Bacher et al. (1996) Proc. Natl. Acad. Sci. USA, 93, 7849-7854.

Bacher, M., Schrader, J., Thompson, N., Kuschela, K., Gemsa, D., Waeber, G., and Schlegel, J. (2003) Am. J. Pathol. 162, 11-17.

Bando, H., Matsumoto, G., Bando, M., Muta, M., Ogawa, T., Funata, N., Nishihira, J., Koike, M., and Toi, M. (2002) Jpn. J. Cancer Res. 93, 389-396.

Bass (2001) Nature 411:428-429.

Basye, J., Trent, J. O., Gao, D., and Ebbinghaus, S. W. (2001) Nucleic Acids Res 29, 4873-80.

Bemis, L., Chan, D. A., Finkielstein, C. V., Qi, L., Sutphin, P. D., Chen, X., Stenmark, K., Giaccia, A. J., and Zundel, W. (2004) Genes Dev. 18, 739-744.

Bendrat et al. (1997) Biochemistry, 36, 15356-15362.

Bendrat, K., Al Abed, Y., Callaway, D. J., Peng, T., Calandra, T., Metz, C. N., and Bucala, R. (1997) Biochemistry 36, 15356-15362.

Bernhagen, J., Mitchell, R. A., Calandra, T., Voelter, W., Cerami, A., and Bucala, R. (1994) Biochemistry. 33, 14144-14155.

Bernstein et al. (2001) Nature 409:363-366.

Bloom et al. (1966) Science, 153:80-82.

Bohm, H. J. (1992) J Comput Aided Mol Des 6, 61-78.

Bucala (1996) FASEB J. 14, 1607-1613.

Bucala (1996) FASEB J., 14, 1607-1613 (1996).

Bucala (1996) The FASEB, Journal 10, 1607-1613.

Buchler, P., Reber, H. A., Lavey, R. S., Tomlinson, J., Buchler, M. W., Friess, H., and Hines, O. J. (2004) J. Surg. Res. 120, 295-303.

Canadian Patent Application No. 2, 359, 180.

Chen, F., Li, Y., Lu, Z., Gao, J., and Chen, J. (2005) Cancer Biol Ther. 4, 1348-1354.

Chesney et al. (1999) Mol. Med., 5, 181-191.

Chesney, J., Metz, C., Bacher, M., Peng, T., Meinhardt, A., and Bucala, R. (1999) J. Immunol., 115, 781-785.

Cornell, W. D., Cieplak, P., Bayly, C. I., Gould, I. R., Merz, K. M., Ferguson, D. M., Spellmeyer, D. C., Fox, T., Caldwell, J. W., and Kollman, P. A. (1995) J. Am. Chem. Soc. 117, 5179-5197.

Cramer, R. D., Patterson, D. E., Clark, R. D., Soltanshahi, F., and Lawless, M. S. (1998) Journal of Chemical Information and Computer Sciences 38, 1010-1023.

Cunha et al. (1993) J. Immunol., 150, 1908-1912.

David (1966) Proc. Natl. Acad. Sci. USA, 56, 72-77.

del Vecchio, M. T., Tripodi, S. A., Arcuri, F., Pergola, L., Hako, L., Vatti, R., and Cintorino, M. (2000) Prostate 45, 51-57.

Dios, A., Mitchell, R. A., Aljabari, B., Lubetsky, J., O'Connor, K., Liao, H., Senter, P. D., Manogue, K. R., Lolis, E., Metz, C., Bucala, R., Callaway, D. J., and Al Abed, Y. (2002) J. Med. Chem. 45, 2410-2416.

Donnelly et al. (1997) Molecular Medicine Today, 3, 502-507.

Elbashir et al. (2001a) Nature 411:494-498.

Elbashir et al. (2001b) Genes Dev 15:188-200.

Eldridge, M. D., Murray, C. W., Auton, T. R., Paolini, G. V., and Mee, R. P. (1997) J Comput Aided Mol Des 11, 425-45.

Epstein, A. C., Gleadle, J. M., McNeill, L. A., Hewitson, K. S., O'Rourke, J., Mole, D. R., Mukherji, M., Metzen, E., Wilson, M. I., Dhanda, A., Tian, Y. M., Masson, N., Hamilton, D. L., Jaakkola, P., Barstead, R., Hodgkin, J., Maxwell, P. H., Pugh, C. W., Schofield, C. J., and Ratcliffe, P. J. (2001) Cell 107, 43-54.

Ewing, T. J., Makino, S., Skillman, A. G., and Kuntz, I. D. (2001) J Comput Aided Mol Des 15, 411-28.

Feltzer, R. E., Trent, J. O., and Gray, R. D. (2003) J Biol Chem 278, 25952-7.

Fingerle-Rowson, G., Petrenko, O., Metz, C. N., Forsthuber, T. G., Mitchell, R., Huss, R., Moll, U., Muller, W., and Bucala, R. (2003) Proc. Natl. Acad. Sci. U.S.A 100, 9354-9359.

Fire et al., (1998) Nature 391:806-811.

Fire (1999) Trends Genet. 15:358-363.

Forsythe, J. A., Jiang, B. H., Iyer, N. V., Agani, F., Leung, S. W., Koos, R. D., and Semenza, G. L. (1996) Mol. Cell. Biol 16, 4604-4613.

Fujii, N., Oishi, S., Hiramatsu, K., Araki, T., Ueda, S., Tamamura, H., Otaka, A., Kusano, S., Terakubo, S., Nakashima, H., Broach, J. A., Trent, J. O., Wang, Z. X., and Peiper, S. C. (2003) Angew Chem Int Ed Engl 42, 3251-3.

Gandara et al. (2002) Semin Oncol 29 (1 Suppl 4), 102-9.

Garcea, G., Neal, C. P., Pattenden, C. J., Steward, W. P., and Berry, D. P. (2005) Eur. J. Cancer 41, 2213-2236.

Gehlhaar, D. K., Verkhivker, G. M., Rejto, P. A., Sherman, C. J., Fogel, D. B., Fogel, L. J., and Freer, S. T. (1995) Chem Biol 2, 317-24.

George et al. (1962) Proc. Soc. Exp. Biol. Med., 111, 514-521.

Gong, Y. and Pauls, H. W. (2000) Synlett 829-831.

Goodsell, D. S., Morris, G. M., and Olson, A. J. (1996). Automated docking of flexible ligands: applications of AutoDock. J. Mol. Recognit. 9, 1-5.

Graeven, U., Rodeck, U., Karpinski, S., Jost, M., Philippou, S., and Schmiegel, W. (2001) Cancer Res. 61, 7282-7290.

Grunstein, J., Roberts, W. G., Mathieu-Costello, O., Hanahan, D., and Johnson, R. S. (1999) Cancer Res. 59, 1592-1598.

Hagen, T., Taylor, C. T., Lam, F., and Moncada, S. (2003) Science 302, 1975-1978.

Hammond et al. (2000) Nature 404:293-296.

Haq, I., Trent, J. O., Chowdhry, B. Z., and Jenkins, T. C. (1999) J. Am. Chem. Soc. 121, 1768-1779.

Hardcastle, I. R., Rowlands, M. G., Houghton, J., Parr, I. B., Potter, G. A., Jarman, M., Edwards, K. J., Laughton, C. A., Trent, J. O., and Neidle, S. (1995) J. Med. Chem. 38, 241-8.

Hira, E., Ono, T., Dhar, D. K., El Assal, O. N., Hishikawa, Y., Yamanoi, A., and Nagasue, N. (2005) Cancer 103, 588-598.

Hudson et al. (1999) J. Exp. Med., 190, 1375-1382.

Jain, A. N. (2003) J. Med. Chem. 46, 499-511.

Janssen, H. L., Haustermans, K. M., Balm, A. J., and Begg, A. C. (2005) Head Neck 27, 622-638.

Jones, G., Willett, P., Glen, R. C., Leach, A. R., and Taylor, R. (1997) J Mol Biol 267, 727-48.

Jorgensen, W. L. (2004) Science 303, 1813-8.

Jung, H., Kim, T., Chae, H. Z., Kim, K. T., and Ha, H. (2001) J Biol. Chem.

Kamimura, A., Kamachi, M., Nishihira, J., Ogura, S., Isobe, H., Dosaka-Akita, H., Ogata, A., Shindoh, M., Ohbuchi, T., and Kawakami, Y. (2000) Cancer 89, 334-341.

Keppler, M. D., Read, M. A., Perry, P. J., Trent, J. O., Jenkins, T. C., Reszka, A. P., Neidle, S., and Fox, K. R. (1999) Eur. J. Biochem. 263, 817-25.

Kleemann, R., Hausser, A., Geiger, G., Mischke, R., Burger-Kentischer, A., Flieger, O., Johannes, F. J., Roger, T., Calandra, T., Kapurniotu, A., Grell, M., Finkelmeier, D., Brunner, H., and Bernhagen, J. (2000) Nature 408, 211-216.

Koong, A. C., Denko, N. C., Hudson, K. M., Schindler, C., Swiersz, L., Koch, C., Evans, S., Ibrahim, H., Le, Q. T., Terris, D. J., and Giaccia, A. J. (2000a) Cancer Res 60, 883-887.

Koong, A. C., Mehta, V. K., Le, Q. T., Fisher, G. A., Terris, D. J., Brown, J. M., Bastidas, A. J., and Vierra, M. (2000b) Int. J. Radiat. Oncol. Biol Phys. 48, 919-922.

Leng, L., Metz, C. N., Fang, Y., Xu, J., Donnelly, S., Baugh, J., Delohery, T., Chen, Y., Mitchell, R. A., and Bucala, R. (2003) J. Exp. Med. 197, 1467-1476.

Liao, H., Bucala, R., and Mitchell, R. A. (2003) J Biol Chem 278, 76-81.

Lipinski, C. A. (2000) J Pharmacol Toxicol Methods 44, 235-49.

Lolis, et al. (1996) Proc. Ass. Am. Phys., 108, 415-419.

Lubetsky et al. (1999) Biochemistry, 38, 7346-7354.

Lubetsky, J. B., Dios, A., Han, J., Aljabari, B., Ruzsicska, B., Mitchell, R., Lolis, E., and Al Abed, Y. (2002) J Biol Chem 277, 24976-24982.

Lubetsky, J. B., Swope, M., Dealwis, C., Blake, P., and Lolis, E. (1999) Biochemistry 38, 7346-7354.

Markert, J. M., Fuller, C. M., Gillespie, G. Y., Bubien, J. K., McLean, L. A., Hong, R. L., Lee, K., Gullans, S. R., Mapstone, T. B., and Benos, D. J. (2001) Physiol Genomics 5, 21-33.

Matsunaga et al. (1999) J. Biol. Chem., 274, 3268-3271.

Matsunaga, J., Sinha, D., Pannell, L., Santis, C., Solano, F., Wistow, G. J., and Hearing, V. J. (1999) J. Biol. Chem. 274, 3268-3271.

McInnes et al. (1988) J. Exp. Med., 167, 598-611.

Menon, C. and Fraker, D. L. (2005) Cancer Lett. 221, 225-235.

Metz et al. (1997) Adv. Immunol. 66, 197-223.

Meyer-Siegler, K., Fattor, R. A., and Hudson, P. B. (1998) Diagn Mol Pathol 7, 44-50.

Meyer-Siegler, K. L., Bellino, M. A., and Tannenbaum, M. (2002) Cancer 94, 1449-1456.

Meyer-Siegler, K. L., Iczkowski, K. A., Leng, L., Bucala, R., and Vera, P. L. (2006) J. Immunol. 177, 8730-8739.

Mikayama et al. (1993) Proc. Natl. Acad. Sci. USA, 90, 10056-10060.

Mitchell, R. A., Metz, C. N., Peng, T., and Bucala, R. (1999) J Biol Chem 274, 18100-18106.

Mitchell, R. A., Liao, H., Chesney, J., Fingerle-Rowson, G., Baugh, J., David, J., and Bucala, R. (2002) Proc. Natl. Acad. Sci. U.S.A 99, 345-350.

Morris, G. M., Goodsell, D. S., Halliday, R. S., Huey, R., Hart, W. E., Belew, R. K., and Olson, A. J. (1998) J. Comp. Chem. 19, 1639-1662.

Nathan et al. (1971) J. Exp. Med., 133, 1356-1376.

Nathan et al. (1973) J. Exp. Med., 137, 275-288.

Naujokas, M. F., Morin, M., Anderson, M. S., Peterson, M., and Miller, J. (1993) Cell 74, 257-268.

Neidle, S., Kelland, L. R., Trent, J. O., Simpson, I. J., Boykin, D. W., Kumar, A., and Wilson, W. D. (1997) Bio. Med. Chem. Lett. 7, 1403-1408.

Nicoletti, F., Creange, A., Orlikowski, D., Bolgert, F., Mangano, K., Metz, C., Di Marco, R., and Al Abed, Y. (2005) J Neuroimmunol. 168, 168-174.

Nunn, C. M., Trent, J. O., and Neidle, S. (1997) FEBS Lett 416, 86-9.

Nykanen et al. (2001) Cell 107:309-321.

Orita, M., Yamamoto, S., Katayama, N., Aoki, M., Takayama, K., Yamagiwa, Y., Seki, N., Suzuki, H., Kurihara, H., Sakashita, H., Takeuchi, M., Fujita, S., Yamada, T., and Tanaka, A. (2001) J. Med. Chem. 44, 540-547.

PCT International Application No. PCT/US02/22010.

PCT International Publication No. WO 99/07409.

PCT International Publication No. WO 99/32619.

PCT International Publication No. WO 00/01846.

PCT International Publication No. WO 00/44895.

PCT International Publication No. WO 00/44914.

PCT International Publication No. WO 00/63364.

PCT International Publication No. WO 01/36646.

PCT International Publication No. WO 01/04313.

PCT International Publication No. WO 01/29058.

PCT International Publication No. WO 01/36646.

PCT International Publication No. WO 01/68836.

PCT International Publication No. WO 01/75164.

PCT International Publication No. WO 01/92513.

PCT International Publication No. WO 02/055692.

PCT International Publication No. WO 02/055693.

PCT International Publication No. WO 02/44321.

Pearlman, R. S. and Smith, K. M. (1999) Abstracts of Papers of the American Chemical Society 217, U698-U698.

Perry, P. J., Reszka, A. P., Wood, A. A., Read, M. A., Gowan, S. M., Dosanjh, H. S., Trent, J. O., Jenkins, T. C., Kelland, L. R., and Neidle, S. (1998) J. Med. Chem. 41, 4873-84.

Petrenko, O., Fingerle-Rowson, G., Peng, T., Mitchell, R. A., and Metz, C. N. (2003) J Biol Chem 278, 11078-11085.

Petrenko, O. and Moll, U. M. (2005) Mol. Cell. 17, 225-236.

Potolicchio, I., Santambrogio, L., and Strominger, J. L. (2003) J Biol Chem 278, 30889-30895.

Pozzi et al. (1992) Cellular Immunol., 145, 372-379.

Priebe, W., Fokt, I., Przewloka, T., Chaires, J. B., Portugal, J., and Trent, J. O. (2001) Methods Enzymol 340, 529-55.

Qu, X., Trent, J. O., Fokt, I., Priebe, W., and Chaires, J. B. (2000) Proc Natl Acad Sci USA 97, 12032-7.

Rarey, M., Kramer, B., Lengauer, T., and Klebe, G. (1996) J Mol Biol 261, 470-89.

Ren, Y., Chan, H. M., Fan, J., Xie, Y., Chen, Y. X., Li, W., Jiang, G. P., Liu, Q., Meinhardt, A., and Tam, P. K. (2006) Oncogene.

Ren, Y., Law, S., Huang, X., Lee, P. Y., Bacher, M., Srivastava, G., and Wong, J. (2005) Ann. Surg. 242, 55-63.

Rendon, B. E., Teneng, I., Zhao, M., Winner, M., Al-Abed, Y., and Mitchell, R. A. (2007). Regulation of human lung adenocarcinoma cell migration and invasion by MIF: Role of Rac1 GTPase and lipid raft assembly. (In revision).

Rice et al. (1998) Annual Reports in Medicinal Chemistry, 33, 243-252.

Rosengren et al. (1996) Mol. Med., 2, 143-149.

Rosengren, E., Aman, P., Thelin, S., Hansson, C., Ahlfors, S., Bjork, P., Jacobsson, L., and Rorsman, H. (1997) FEBS Lett. 417, 85-88.

Rosengren, E., Bucala, R., Aman, P., Jacobsson, L., Odh, G., Metz, C. N., and Rorsman, H. (1996) Mol. Med. 2, 143-149.

Ryan, H. E., Lo, J., and Johnson, R. S. (1998) EMBO J. 17, 3005-3015.

Sakamoto, T., Sakasai, T., and Yamanaka, H. (1980) Chemical & Pharmaceutical Bulletin 28, 571-577.

Sakaue et al. (1999) Mol. Med., 5, 361-371.

Sawayama, T., Yamamoto, R., Kinugasa, H., and Nishimura, H. (1977) Heterocycles 8, 299-305.

Saygili, N., Batsanov, A. S., and Bryce, M. R. (2004) Org. Biomol. Chem. 2, 852-857.

Senter, P. D., Al Abed, Y., Metz, C. N., Benigni, F., Mitchell, R. A., Chesney, J., Han, J., Gartner, C. G., Nelson, S. D., Todaro, G. J., and Bucala, R. (2002) Proc. Natl. Acad. Sci. U.S.A 99, 144-149.

Shannon, A. M., Bouchier-Hayes, D. J., Condron, C. M., and Toomey, D. (2003) Cancer Treat. Rev. 29, 297-307.

Shi, X., Leng, L., Wang, T., Wang, W., Du, X., Li, J., McDonald, C., Chen, Z., Murphy, J. W., Lolis, E., Noble, P., Knudson, W., and Bucala, R. (2006) Immunity. 25, 595-606.

Shimizu, T., Abe, R., Nakamura, H., Ohkawara, A., Suzuki, M., and Nishihira, J. (1999) Biophys. Res. Commun. 264, 751-758.

Shun, C. T., Lin, J. T., Huang, S. P., Lin, M. T., and Wu, M. S. (2005) World J Gastroenterol. 11, 3767-3771.

Singh, S., Powell, D. W., Rane, M. J., Millard, T. H., Trent, J. O., Pierce, W. M., Klein, J. B., Machesky, L. M., and McLeish, K. R. (2003) J Biol Chem 278, 36410-7.

Sugimoto, H., Suzuki, M., Nakagawa, A., Tanaka, I., and Nishihira, J. (1996) FEBS Lett. 389, 145-148.

Sugimoto et al. (1999) Biochemistry, 38, 3268-3279.

Sun, B., Nishihira, J., Yoshiki, T., Kondo, M., Sato, Y., Sasaki, F., and Todo, S. (2005) Clin. Cancer Res. 11, 1050-1058.

Sun, H. W., Bernhagen, J., Bucala, R., and Lolis, E. (1996) Proc. Natl. Acad. Sci. U.S.A 93, 5191-5196.

Swant, J. D., Rendon, B. E., Symons, M., and Mitchell, R. A. (2005) J Biol Chem 280, 23066-23072.

Swope et al. (1998) EMBO J., 17, 3534-3541.

Swope et al. (1999) Rev. Physiol. Biochem. Pharmacol. 139, 1-32.

Swope, M., Sun, H. W., Blake, P. R., and Lolis, E. (1998) EMBO J. 17, 3534-3541.

Taetle, R., Rosen, F., Abramson, I., Venditti, J., and Howell, S. (1987) Cancer Treat. Rep. 71, 297-304.

Takahashi, N., Nishihira, J., Sato, Y., Kondo, M., Ogawa, H., Ohshima, T., Une, Y., and Todo, S. (1998) Mol. Med. 4, 707-714.

Tamamura, H., Hiramatsu, K., Kusano, S., Terakubo, S., Yamamoto, N., Trent, J. O., Wang, Z., Peiper, S. C., Nakashima, H., Otaka, A., and Fujii, N. (2003a) Org Biomol Chem 1, 3656-62.

Tamamura, H., Hiramatsu, K., Mizumoto, M., Ueda, S., Kusano, S., Terakubo, S., Akamatsu, M., Yamamoto, N., Trent, J. O., Wang, Z., Peiper, S. C., Nakashima, H., Otaka, A., and Fujii, N. (2003b) Org Biomol Chem 1, 3663-9.

Tamamura, H., Mizumoto, M., Hiramatsu, K., Kusano, S., Terakubo, S., Yamamoto, N., Trent, J. O., Wang, Z., Peiper, S. C., Nakashima, H., Otaka, A., and Fujii, N. (2004) Org Biomol Chem 2, 1255-7.

Taylor, A. B., Johnson, W. H., Jr., Czerwinski, R. M., Li, H. S., Hackert, M. L., and Whitman, C. P. (1999) Biochemistry 38, 7444-7452.

Thomsen, R. and Christensen, M. H. (2006) J. Med. Chem. 49, 3315-3321.

Thorpe, D. S., Edith Chan, A. W., Binnie, A., Chen, L. C., Robinson, A., Spoonamore, J., Rodwell, D., Wade, S., Wilson, S., Ackerman-Berrier, M., Yeoman, H., Walle, S., Wu, Q., and Wertman, K. F. (1999) Biochem Biophys Res Commun 266, 62-5.

Thurman et al., (1985) J. Immunol., 134, 305-309.

Trent, J. O. and Neidle, S. (1996). Molecular Modeling of Drug-DNA Interactions:Facts or Fantasies. In Advances in Sequence specific agents, L. Hurley, ed. JAI Press Inc), pp. 29-58.

Trent, J. O., Clark, G. R., Kumar, A., Wilson, W. D., Boykin, D. W., Hall, J. E., Tidwell, R. R., Blagburn, B. L., and Neidle, S. (1996) J Med Chem 39, 4554-62.

Trent, J. O. (2001) Methods in Enzymology 340.

Trent, J. O., Wang, Z. X., Murray, J. L., Shao, W., Tamamura, H., Fujii, N., and Peiper, S. C. (2003) J Biol Chem 278, 47136-44.

Tsuzuki, Y., Fukumura, D., Oosthuyse, B., Koike, C., Carmeliet, P., and Jain, R. K. (2000) Cancer Res. 60, 6248-6252.

U.S. Pat. No. 6,506,559.

Venkatachalam, C. M., Jiang, X., Oldfield, T., and Waldman, M. (2003) Mol Graph Model 21, 289-307.

Wadgaonkar, R., Dudek, S. M., Zaiman, A. L., Linz-McGillem, L., Verin, A. D., Nurmukhambetova, S., Romer, L. H., and Garcia, J. G. (2005) J Cell Biochem. 95, 849-858.

Walters, W. P., Ajay, and Murcko, M. A. (1999) Curr Opin Chem Biol 3, 384-7.

Walters, W. P. and Murcko, M. A. (2002) Adv Drug Deliv Rev 54, 255-71.

Wang, G. T., Wang, S., Gentles, R., Sowin, T., Leitza, S., Reilly, E. B., and von Geldern, T. W. (2005) Bioorg. Med. Chem. Lett. 15, 195-201.

Weiser, et al. (1981) J. Immunol. 126, 1958-1962.

Weiser et al. (1989) Proc. Natl. Acad. Sci. USA, 86, 7522-7526.

Weiser et al. (1991) J. Immunol., 147, 2006-2011.

Weiser et al. (1992) Proc. Natl. Acad. Sci. USA, 89, 8049-8052.

White, E. S., Strom, S. R., Wys, N. L., and Arenberg, D. A. (2001) J. Immunol. 166, 7549-7555.

Wianny & Zernicka-Goetz (1999) Nature Cell Biol 2:70-75.

Wilson, J. M., Coletta, P. L., Cuthbert, R. J., Scott, N., MacLennan, K., Hawcroft, G., Leng, L., Lubetsky, J. B., Jin, K. K., Lolis, E., Medina, F., Brieva, J. A., Poulsom, R., Markham, A. F., Bucala, R., and Hull, M. A. (2005) Gastroenterology 129, 1485-1503.

Winner, M., Koong, A. C., Rendon, B. E., Zundel, W., and Mitchell, R. A. (2007) Cancer Res. 67, 186-193.

Zeman et al. (1986) Int J Radiat Oncol Biol Phys 12 (7), 1239-42.

Zhong, H. and Bowen, J. P. (2006) Curr. Med. Chem. 13, 849-862.

Zundel, W., Schindler, C., Haas-Kogan, D., Koong, A., Kaper, F., Chen, E., Gottschalk, A. R., Ryan, H. E., Johnson, R. S., Jefferson, A. B., Stokoe, D., and Giaccia, A. J. (2000) Genes Dev. 14, 391-396.

What is claimed is:

1. A method of inhibiting a biological activity of a Macrophage migration inhibitory factor (MIF) polypeptide, comprising contacting the MIF polypeptide with a compound having a structure of Formula (I):

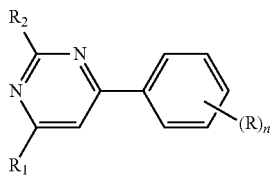

wherein:
each R is independently H, halo, OH, alkyl, substituted alkyl, aryl, amino, or carboxyl;
$R_1$ is iodo;
$R_2$ is H, halo, OH, alkyl, substituted alkyl, aryl, or amino; and
n is an integer from 0 to 5.

2. The method of claim 1, wherein the compound forms a stable interaction with at least a methionine at the second N-terminal residue (Met-2) of the MIF polypeptide.

3. The method of claim 2, wherein the MIF polypeptide comprises a homotrimer of monomers A, B, and C, and monomer A comprises the Met-2(Met-A2).

4. The method of claim 3, wherein the compound further forms a stable interaction with one or more of Pro-1, Lys-32, Pro-33, Tyr-36, His-62, Ser-63, Ile-64, Lys-66, Tyr-95, Met-101, Val-106, Trp-108 and Phe-113 of the MIF polypeptide.

5. The method of claim 1, wherein the MIF polypeptide is a mammalian MIF polypeptide.

6. The method of claim 5, wherein the MIF polypeptide comprises SEQ ID NO:1.

7. A method for inhibiting a biological activity of a Macrophage migration inhibitory factor (MIF) polypeptide, comprising contacting the MIF polypeptide with 4-iodo-6-phenylpyrimidine.

* * * * *